United States Patent
Wu

(10) Patent No.: US 11,576,945 B2
(45) Date of Patent: Feb. 14, 2023

(54) TREATMENT FOR ISCHEMIC STROKE

(71) Applicant: CHS Pharma Inc., Naples, FL (US)

(72) Inventor: Jang-Yen Wu, Boca Raton, FL (US)

(73) Assignee: CHS PHARMA INC., Hallandale Beach, FL (US)

( * ) Notice: Subject to any disclaimer, the term of this patent is extended or adjusted under 35 U.S.C. 154(b) by 51 days.

(21) Appl. No.: 17/149,564

(22) Filed: Jan. 14, 2021

(65) Prior Publication Data

US 2021/0138021 A1 May 13, 2021

Related U.S. Application Data

(63) Continuation of application No. PCT/US2019/043451, filed on Jul. 25, 2019.

(60) Provisional application No. 62/703,687, filed on Jul. 26, 2018.

(51) Int. Cl.
*A61K 38/06* (2006.01)
*A61P 9/10* (2006.01)
*A61K 9/00* (2006.01)

(52) U.S. Cl.
CPC .......... *A61K 38/063* (2013.01); *A61K 9/0019* (2013.01); *A61P 9/10* (2018.01)

(58) Field of Classification Search
None
See application file for complete search history.

(56) References Cited

U.S. PATENT DOCUMENTS

| | | | |
|---|---|---|---|
| 6,156,794 A | 12/2000 | Faiman | |
| 7,250,401 B2 * | 7/2007 | Schloss | C07K 5/0215 514/17.7 |
| 7,723,302 B2 | 5/2010 | Wu | |
| 9,050,305 B2 | 6/2015 | Wu | |
| 9,827,220 B2 | 11/2017 | Wu et al. | |
| 10,272,063 B2 | 4/2019 | Wu | |
| 2005/0119262 A1 | 6/2005 | Wax | |
| 2012/0295979 A1 | 11/2012 | Prentice | |
| 2015/0265569 A1 * | 9/2015 | Wu | A61K 31/27 514/479 |

FOREIGN PATENT DOCUMENTS

| | | |
|---|---|---|
| RU | 2284190 | 9/2006 |
| WO | 2012/106654 | 8/2012 |

OTHER PUBLICATIONS

Faiman, Morris D. et al., "S-(N, N-diethylcarbamoyl)glutathione (carbamathione), a disulfiram metabolite and its effect on nucleus accumbens and prefrontal cortex dopamine, GABA, and glutamate: A microdialysis study," Neuropharmacology, Dec. 2013, No. 75:95-105.

Modi, Jigar: "Mechanism of carbamathione as a therapeutic agent for stroke," Florida Atlantic University, Dec. 2017:1-8.

Dmitrievich, Genkin Dmitrij et al.: "Method for Treating Ischemic Cardiac Disease, or Myocardial Infraction and its Aftereffects, or Cerebral Ischemia Induced by Atherosclerosis or Acute Dysfunction of Cerebral Circulation, and its Aftereffects, or Atherosclerosis-Induced Ischemia of Inferior Limbs," RU patent No. 2284190 (C1), Sep. 27, 2006, (English Abstract only).

Chapman, Kristine M., et al: "Intravenous Tissue Plasminogen Activator for Acute Ischemic Stroke," Stroke, 2000, No. 31:2920-2924.

Miodi, Jigar: "Protective Mechanism of Sulindac Against Animal Model of Ischemic Stroke," Thesis submitted to the faculty of The Charles E. Schmidt College of Medicine, Florida Atlantic University, Dec. 2011: 1-58.

* cited by examiner

*Primary Examiner* — Christina Bradley
(74) *Attorney, Agent, or Firm* — Stanley A. Kim

(57) ABSTRACT

Carbamathione agent protects brain tissue exposed to a cerebral ischemia/reperfusion injury, and minimizes the size of infarcts that develop as a result of the injury.

8 Claims, 25 Drawing Sheets a)

b)

a)

b)

a)

b)

c)

a)

b)

a)

b)

a)

b)

a)

b)

a)

b)

a)

b)

a)

b)

TREATMENT FOR ISCHEMIC STROKE

CROSS-REFERENCE TO RELATED APPLICATIONS

The present application is a by-pass continuation under 35 U.S.C. 111(a) of international patent application number PCT/US2019/043451 filed on Jul. 25, 2019, which claims priority from U.S. provisional patent application No. 62/703,687, filed on Jul. 26, 2018.

STATEMENT AS TO FEDERALLY SPONSORED RESEARCH

Not applicable.

FIELD OF THE INVENTION

The invention relates generally to the fields of neurology, pharmaceuticals, and medicine. More particularly, the invention relates to the use of agents to protect brain tissue from ischemia/reperfusion injury.

BACKGROUND

Stroke is the leading cause of disability and the third leading cause of death in the USA. Much progress has been made regarding the mechanism of brain injury induced by ischemia/hypoxia, a major pathophysiology of stroke. It is generally believed that excitotoxicity caused by excessive release of excitatory neurotransmitter glutamate plays an important role in ischemia/reperfusion induced neuronal death. Despite extensive research to develop medicines for stroke based on the known mechanisms either as glutamate receptor antagonists, Ca2+ channel blockers, enzyme inhibitors, inhibitors of apoptotic pathways, or ROS scavengers, etc., these efforts have been disappointing. Part of the reason for the disappointing results is due to the fact that the underpinning mechanism of stroke-induced neuronal injury is multi-factorial and hence it needs a therapeutic intervention that addresses the multi-factorial nature of the disease.

SUMMARY

It has been discovered that carbamathione [S—(N,N-diethylcarbamoyl)glutathione] is effective at protecting brain tissue exposed to a cerebral ischemia/reperfusion injury, and for minimizing the size of infarcts that develop as a result of the injury. This discovery led to the development of a method for minimizing the size of a brain infarct which develops (or reducing the amount of brain tissue damaged) in a mammalian subject as a consequence of a cerebral ischemia/reperfusion injury. This method can include the step of administering to the subject at least one (e.g., 1, 2, or 3) dose of a carbamathione agent wherein the amount of the agent administered is effective for minimizing the size of a brain infarct that develops in a mammalian subject as a consequence of the cerebral ischemia/reperfusion injury. In this method, the subject can be a human being who has been diagnosed with ischemic stroke prior to the administration step and/or one that has been administered tissue plasminogen activator or another thrombolytic. The carbamathione agent can be included within a pharmaceutical composition formulated for injection, can be administered to the subject within 24 hours of the onset of symptoms of ischemic stroke, can be repeatedly administered to the subject at least once per day for at least 3 or at least 7 days or until the infarcted lesion becomes at least 50% fibrotic.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
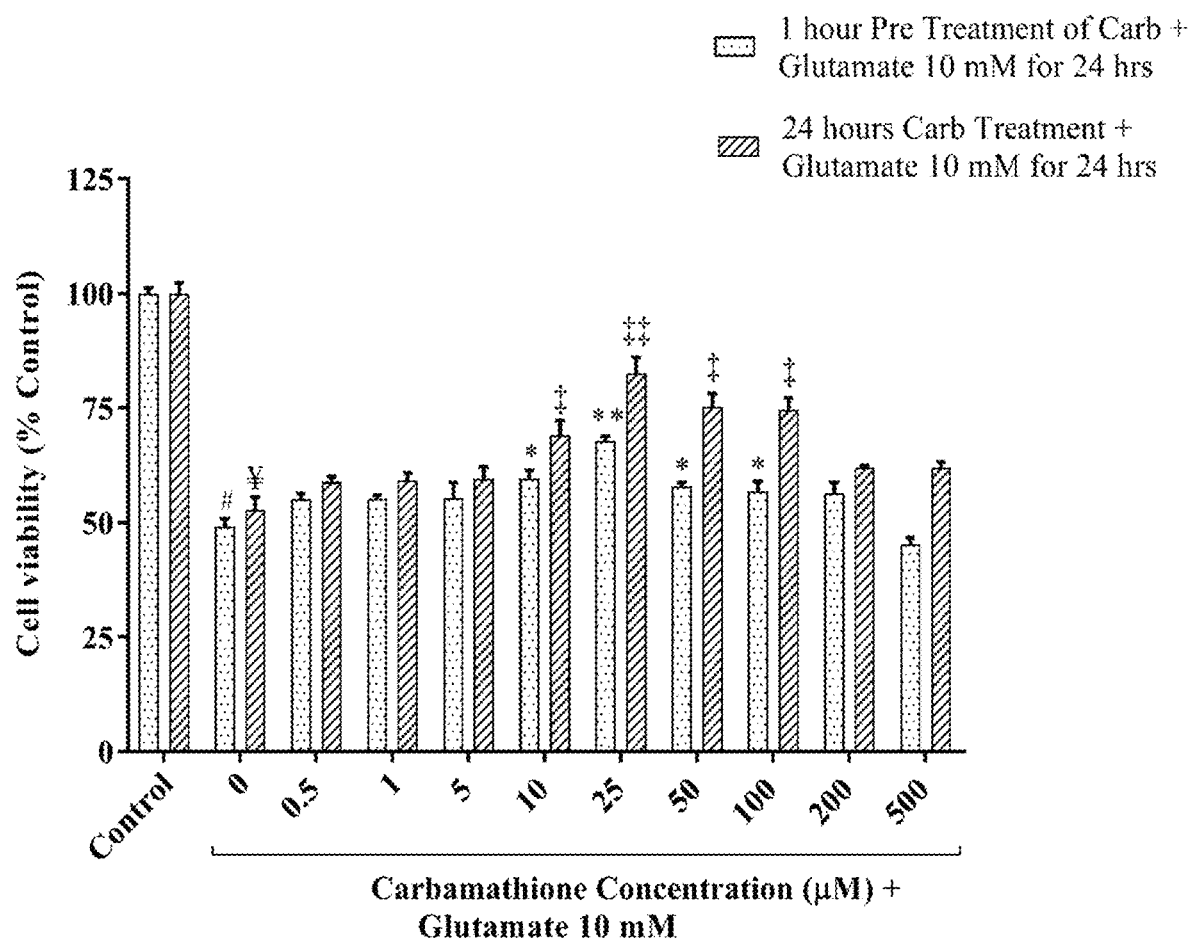
FIG. 1 is a graph showing the effect of carbamathione on glutamate induced injury of PC-12 cells.

The invention provides methods and compositions for treating stroke, protecting brain tissue, and minimizing the size of a brain infarct caused by ischemia/reperfusion injury in a mammalian subject. The below described embodiments illustrate representative examples of these methods and compositions. Nonetheless, from the description of these embodiments, other aspects of the invention can be made and/or practiced based on the description provided below.

General Methods

Methods involving conventional organic chemistry, medicinal chemistry, pharmaceutical sciences, and drug development techniques are described herein. Such methods are described in: Remington: The Science and Practice of Pharmacy, Lippincott Williams & Wilkins, 21st edition (2005); Drug Discovery and Development, Mukund S. Chorghade (Editor) Wiley-Interscience; 1st edition (2007); The Practice of Medicinal Chemistry, 3rd Edition, (Editor) Academic Press; 3rd edition (2008); and Clayden et al., Organic Chemistry, Oxford University Press, 1st edition (2000). Method in neurology are described in Bradley's Neurology in Clinical Practice, 6th Edition, Elsevier (2012).

Methods of Treating Ischemic Stroke

Methods of treating ischemic stroke and other ischemic neurologic injuries (e.g., those caused by subarachnoid hemorrhage), or minimizing the size of a brain infarct caused by ischemia/reperfusion injury in a mammalian subject can include the step of administering one or more (e.g., 1, 2, or 3) doses of a carbamathione agent to the subject in an effective amount or amounts to minimize the size of a brain infarct resulting from the injury. Effective derivatives and analogues of carbamathione might also be used in such methods. The effectiveness of such derivatives and analogues can be confirmed by the methods described herein. The carbamathione agent can be formulated as a separate pharmaceutical composition, or in combination with other agents used to treat stroke.

The subject can be a mammal such as a human being, a rodent, a cat, a dog, a horse, a sheep, or a pig having or at risk for developing ischemic stroke or a brain infarct (e.g., a subject experiencing one or more transient ischemic attacks). As a non-limiting example, the subject can be a human being diagnosed with cerebral vessel occlusion or one having transient ischemic attacks. The subject can also be a human being who has been administered tissue plasminogen activator (e.g., following being diagnosed with acute cerebral vessel occlusion). The initial dose of the carbamathione agent can be administered within 1, 2, 3, 4, 5, 6, 7, 8, 9, 10, 11, 12, 13, 14, 15, 16, 17, 18, 19, 20, 24, 36, or 48 h of the onset of symptoms of ischemic stroke. For a subject at high risk for developing an ischemic stroke (e.g., subject experiencing transient ischemic attacks or having a thrombosis), the carbamathione agent can be administered prophylactically, with a frequency of four times per day, thrice per day, twice per day, once a day, or once every 2, 3, 4, 5, 6, 7, or 14 days until the risk is decreased (e.g., transient ischemic attacks stop or the thrombosis is cleared).

The pharmaceutical formulation can be administered to the subject by any suitable method including orally, topically, by injection (e.g., intravenous, subcutaneous, intraperitoneal, or intrathecal injection; injection into an IV bag in fluid communication with a blood vessel in the subject; and infusion such as through a catheter), or implanting a slow-release depot device. For oral formulations, administrations can be, without limitation, four times per day, thrice per day, twice per day, once a day, or once every 2, 3, 4, 5, 6, 7, 14, 28, 35, 42, or 49 days (or until the ischemia/reperfusion-induced lesion becomes at least 50, 60, 70, 80, 90, or 100% fibrotic or acellular). For injectable formulations, administrations can be, without limitation, 100 µl to 100 ml (e.g., 100 µl, 500 µl, 1 ml, 2 ml, 3, ml, 4 ml, 5 ml, 10, ml, 20 ml, 50 ml, or 100 ml) four times per day, thrice per day, twice per day, once a day; or once every 2, 3, 4, 5, 6, 7, 14, 28, 35, 42, or 49 days (or until the ischemia/reperfusion-induced lesion becomes at least 50, 60, 70, 80, 90, or 100% fibrotic or acellular). Other possible methods of administration include intra-nasal (e.g., via a liquid spray, such as via a plastic bottle atomizer), inhalation or insufflation (e.g., of a dry powder formulation), and mucosal (rectal, vaginal, or buccal). Administration can continue indefinitely or until the infarct is completely formed or the factors causing an elevate risk for developing an ischemic stroke are removed. Brain lesions/infarcts can be monitored by methods known in the art, e.g., CT scanning.

The effective amount of the carbamathione agent may be delivered in multiple doses, preferably within about three hours of the sudden onset of neurological symptoms associated with stroke. The effective amount of the carbamathione agent may be delivered in combination with ongoing administration of aspirin to reduce the risk of blood clot formation, or administration of other agents to improve blood flow by reducing the formation of clots or dissolving blood clots (e.g., estrogen, eNOS inducer, L-arginine, a statin, aspirin, tissue plasminogen activator, modified viper venom, and prourokinase). In addition, agents and devices for controlling and regulating blood flow may also be used in combination with the carbamathione agent to treat stroke or stroke-like events.

Pharmaceutical Formulations

The carbamathione agent can be included along with one or more pharmaceutically acceptable carriers or excipients to make pharmaceutical compositions which can be administered to the subject. Suitable formulations for use in the present invention are described in Remington's Pharmaceutical Sciences, Mace Publishing Company, Philadelphia, Pa., 17th ed. (1985) and updates thereto.

In pharmaceutical compositions including carbamathione or derivatives or analogues of carbamathione ("carbamathione agents"), the carbamathione agent can be included as at least 0.01% (e.g., at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, or 10%) by weight of the formulation. The dose of the carbamathione agent per administration can be in the range of 0.2 to 20 mg/kg (preferably 1-10 mg/kg).

The pharmaceutical composition(s) might also be formulated for injection and administered by injection. Such compositions can have a pH of between 6.5 and 8.5 or between 6.8 and 7.8. Excipients/carriers/other ingredients can include a sterile aqueous buffer, an isotonizing agent, a microbicidal agent or preservative, a chelating agent, a solubility enhancing agent such as dimethylsulfoxide, and/or other ingredients. The isotonizing agent can be, e.g., sorbitol, glycerine, polyethylene glycol, propylene glycol, glucose and sodium chloride. The microbicidal agent/preservative can be, e.g., para-oxybenzoic acid esters, benzyl alcohol, para-chloro-meta-xylenol, chlorocresol, phenetyl alcohol, sorbic acid and salts thereof, thimerosal, chlorobutanol, etc. The chelating agent can be, for example, sodium edetate, sodium citrate or the sodium salt of condensed phosphoric acid.

The pharmaceutical composition can also be included in an implantable slow-release depot device that can be placed in the subject (e.g., at a subcutaneous position) by surgical techniques. In such devices, the carbamathione agent can be manufactured into microparticles (e.g., with a particle size of 1 to 200 microns) which are embedded in a biocompatible pharmacologically acceptable polymer or a lipid encapsulating agent. The depot formulations can be designed to release all or substantially all the active material over an extended period of time, e.g. several weeks up to 6 months. The matrix, e.g. polymer or lipid matrix, if present, is adapted to degrade sufficiently to be transported from the site of administration within one to 6 months after release of all or substantially all the active agent.

To enhance half-life, the carbamathione agent may be encapsulated, introduced into the lumen of liposomes, prepared as a colloid. A variety of methods are available for preparing liposomes, as described in, e.g., Szoka, et al., U.S. Pat. Nos. 4,235,871, 4,501,728 and 4,837,028 each of which is incorporated herein by reference. The carbamathione agent may also be formulated for parenteral administration and presented in unit dosage form in ampules, prefilled syringes, small volume infusion containers or multi-dose containers with an added preservative.

EXAMPLES

Example 1—Materials and Methods

PC-12 cells (purchased from ATCC, Manassas, Va., USA) were cultured in a petri dish for one week prior to use. PC-12 cells were maintained at 37° C./5% CO2 in an incubator, and fed every other day using F12-K medium supplemented with 5% (v/v) fetal bovine serum (FBS), 10% (v/v) heat-inactivated horse serum (HS) and 1% (v/v) penicillin-streptomycin solution. Experiments were performed on undifferentiated cells plated in 96-well plates at a density of approximately $5 \times 10^4$ cells/ml for the ATP assay. On first day of use, cells were harvested by first adding 2 mL trypsin and incubated for 15 minutes. 2 mL fresh medium was then used as a wash and cells were spun, and re-suspended. Cell density was determined by cell counting using a hemocytometer and a tissue culture microscope. After cell density was determined, 96-well plates and 6-well plates were plated with $2.5 \times 10^4$ cells per well and $5 \times 10^5$ cells per well for the adenosine 5'-triphosphate (ATP) assay and Western blot analysis, respectively.

Cell cultures were preincubated with 0.5 μM to 500 μM concentration of carbamathione for one hour. Ten mM glutamate was added, and the plates were cultured for 24 hours in a hypoxia chamber with oxygen levels maintained at 0.3-0.4%. Reoxygenation was performed by removing the plates from the hypoxic chamber and transferring them into normoxic culture incubator for another 24 hours. For the ATP assay, ATP solution was added to each well, and cells were incubated for 10 min after which time the amount of ATP was quantified through a luciferase reaction. The luminescence intensity was determined using a luminometer with lysates in a standard opaque-walled multi-well plate. The ATP content was determined by running an internal standard and expressed as a percentage of untreated cells (control).

For the bilateral carotid artery occlusion assay (BCAO) experiments, male Swiss Webster mice (20 weeks of age) were obtained from Charles River laboratory. The mice were allowed access to water only and kept fasting overnight before surgery. Mice were anesthetized with ketamine (100 mg/kg, i.p.) plus xylazine (10 mg/kg, i.p.). For induction of anesthesia, mice were exposed to a gaseous mixture consisting of 30% oxygen, 70% $N_2O$ and 0.5% isoflurane using a vaporizer. For maintenance of anesthesia, isoflurane concentration was used to 0.5%. Mice were breathing spontaneously via breathing mask throughout the surgical procedure. A rectal temperature probe was inserted. During surgery, mice were resting on a thermostat-controlled heating pad, ensuring a constant core temperature of 37.0±0.5° C.

While anesthesia was maintained as described above, each mouse was placed on its back, and its tail and paws were fixed to the heating pad using adhesive tape. A sagittal ventral midline incision (~1 cm length) was performed. Both common carotid arteries (CCAs) were isolated, freed of nerve fibers, and occluded using non-traumatic aneurysm clips. Complete interruption of blood flow was confirmed under an operating microscope. After 30 min of ischemia, the aneurysm clips were removed from both CCAs. Restoration of blood flow (reoxygenation) was observed directly under the microscope. Sham-operated controls were subjected to the same surgical procedures except that CCAs were not occluded. The body temperature was monitored and maintained at 37° C.±0.5° C. during the immediate postoperative period until the animals recovered fully from anesthesia.

The Corner test, which determines an animal's asymmetric direction of turning when encountering a corner, is used as an indicator of brain injury. An experimental corner setup composed of two boards (with dimensions of 30×20×1 cm$^3$) was arranged to form a 30° corner; a small opening was left along the joint between the two boards. Each mouse was placed 12 cm from the corner and allowed to walk into the corner, so that the vibrissae on both sides of the animal's face contacted the two boards simultaneously. Before the BCAO procedure, behavior tests (stratification) were conducted on all mice to screen for mice with no turning asymmetry (n≥18). Each mouse took part in ten trials, after which we calculated the percentage of turns to each side, recording only those turns involving full rearing along one of the boards. This stratification procedure excludes mice with 80-100% asymmetric turns (n=4); only mice that turned in either direction (n=14) with a pretest score of 0.50±0.08 were used in subsequent experiments. Each mouse took part in ten trials for up to 4 days after BCAO.

The force-plate actometer is an ensemble of mechanical, electronic, and computing elements that embody mathematical and physical principles to produce measurement of whole-organism behavioral attributes of relevance to basic neuroscience research. Briefly, the force-plate actometer purchased from BASi Corp (model FPA-I; West Lafayette, Ind., USA) consists of a force-sensitive plate at a resolution of 200 Hz, a sound attenuation chamber, a computerized data acquisition board, and an analysis system software (FPA 1.10.01). A newly-developed force-plate actometer was utilized to measure locomotor activity. Animals were placed on the force plate actometer for one separate 60 min sessions. Locomotor activity assays with and without carbamathione treatment were performed 4 days after BCAO. Trace data of movements were automatically stored on the hard drive for off-line analysis. Changes in locomotion were revealed through power spectral analysis and expressed as arbitrary distance. The unit for changes in the power force was arbitrary.

Animals were randomly assigned for sham, control, and experimental groups. Thereafter, in experimental group (carbamathione treated group, N=9), carbamathione (14 mg/kg in 0.3 mL saline 0.9%) was injected subcutaneously 30 min after occlusion and continued daily until the animal was sacrificed. In control groups (vehicle-treated group, N=9), vehicle (0.3 ml saline 0.9%) was injected subcutaneously 30 min after occlusion. Sham-operated group (N=6) received the same surgical procedure without occlusion of common carotid artery. After surgery, animals were allowed to recover from the anesthesia, and given food and water ad libitum. The animals were daily examined for body temperature and weight, and those who had body temperature more than 39° C. after 24 hour were excluded from the experiment.

Mice were euthanized 4 days after surgery. The brain was quickly removed and sectioned into 2 mm thick slices starting at the frontal pole using a Brain Matrix Slicer (Zivic instruments, PA, USA). Slices were immersed in 2% TTC (J. C. Baker, India) in a Petri dish and incubated at 37° C. for 5 minutes. TTC, a water-soluble salt, is reduced by mitochondrial dehydrogenases to formazan, a red, lipid-soluble compound that turns normal tissue deep red. Thus, reduced TTC staining identifies regions of diminished mitochondrial function in the ischemic tissue. To assess lesion volume, TTC-stained slices (2, 4, 6, 8, and 10 mm from the frontal pole) were scanned using a scanner and analyzed by Image-J analysis software. Lesion volume was determined as the percent of the total both hemispheric volume and was calculated as:

$$[(V_C - V_L)/V_C]100$$

where VC is the volume of the both hemispheres (compared to the value with whole brain of sham) and VL is the volume of non-lesioned tissue in the lesioned hemisphere. These sections were then compared among the different treated and untreated animal groups.

For the Western blot assays, animals were deeply anesthetized by isoflurane (Phoenix) and decapitated, and then brains were rapidly removed. After sacrifice, the while the brain was on ice, the left hemisphere and the right hemisphere (identical parts) were quickly dissected on dry ice and homogenized in Lysis buffer consisting of 50 mM Tris-HCl, 150 mM NaCl, 2 mM EDTA, pH 8.0, 1% Triton-X-100, 1:100 dilution of mammalian protease inhibitors (Sigma-Aldrich, MO, USA) and protease inhibitor for immunoblotting. Protein concentrations of each sample solution were determined with a Bradford protein assay, and samples were stored at −80° C. until use. Protein samples were separated by 12% sodium dodecyl sulfate-polyacrylamide gel electrophoresis and transferred onto nitrocellulose membranes. Western blot was performed using the following primary antibodies overnight: abcam: GRP 78, HSP70, HSP 27, activating transcription factor 4 (ATF4), and X-box-binding protein 1 (XBP-1) (1:500); Cell Signaling: GAPDH (1:3,000), Bax, BCL2 (1:1,000), AKT, phosphorylated AKT (p-AKT); Santa Cruz: CHOP/GADD153); Imgenex: ATF6 (1:1,500). The membranes were washed three times with Tris-buffered saline containing 0.1% Tween-20 (TBS-T) and incubated with secondary antibodies for 1 hour at room temperature. Secondary antibodies used were goat IRDye 800-conjugated anti-rabbit (1:15,000) and IRDye 680 conjugated anti-mouse (1:15,000) antibodies (LI-COR Biosciences, Lincoln, Nebr., USA). Fluorescent signals were detected with a LI-COR Odyssey Fc system and the images were quantified with the provided either Image Studio 2.0 software or image J software.

All data were expressed as the mean±SEM. A computer program (SPSS 15.0, Chicago, Ill., USA and Prism Graph Pad 7) was used for statistical analysis. The statistical significance of the data was determined with t-test or one-way ANOVA combined with Dunnett post-hoc or Tukey test for comparison between groups. Differences of P<0.05 were considered statistically significant. At least three independent replicates were performed for each experiment.

Example 2—Results

PC-12 cells were exposed to different concentrations of glutamate in a range of 0.01 mM to 150 mM for 24 hours, then the ATP assay was performed. At 10 mM glutamate, about 45% of survival PC-12 cells was observed. This dose was selected for in vitro PC-12 cell assays described below. To determine whether carbamathione exerted a protective effect in glutamate toxicity in PC-12 cells, referring to FIG. 1, cell viability was measured by ATP assay where PC-12 cells were exposed to 0.5 μM to 500 μM carbamathione for 1 or 24 h before 10 mM glutamate treatment for 24 hours. (All data are presented as mean+/−SEM, where #/*/‡/¥/ p<0.05, ‡‡/**p<0.01, */‡ significant with glutamate 10 mM group, #/¥ statistical significance with control group). As shown in FIG. 1, at most concentrations and treatment periods carbamathione increased the survival of PC-12 cells in the assay.

Figure 2:
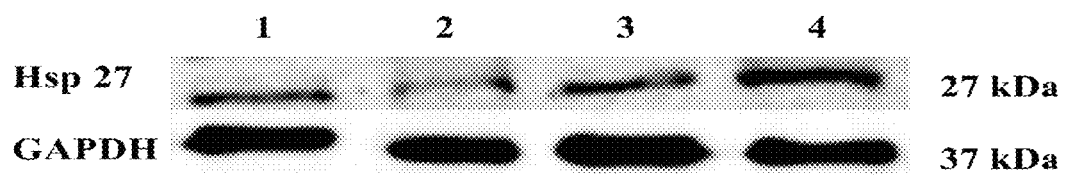
FIG. 2 is a Western blot (a) and graph (b) showing Hsp expression in PC-12 cells after glutamate exposure with or without treatment with carbamathione.
Figure 2:
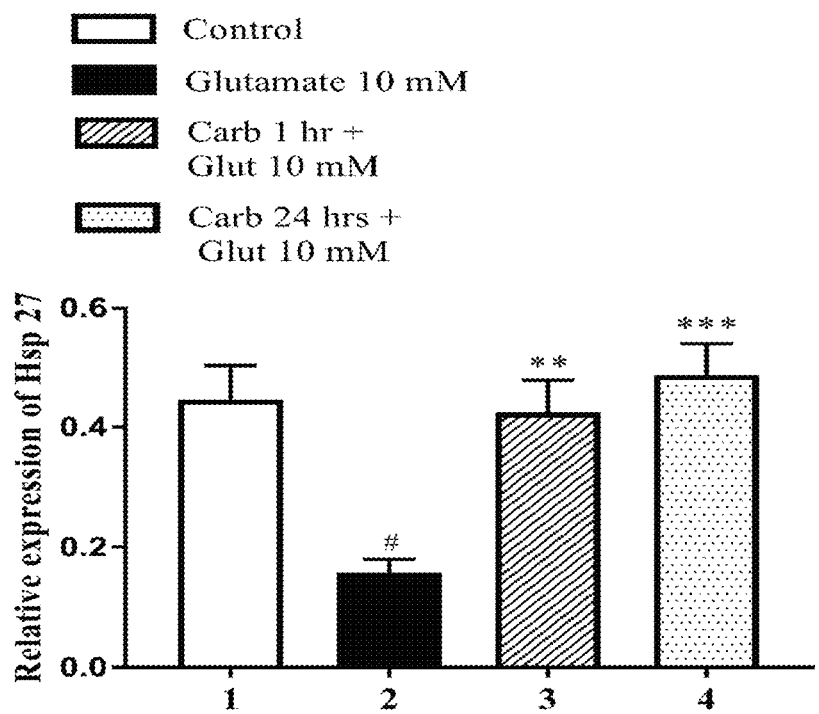
Figure 3:
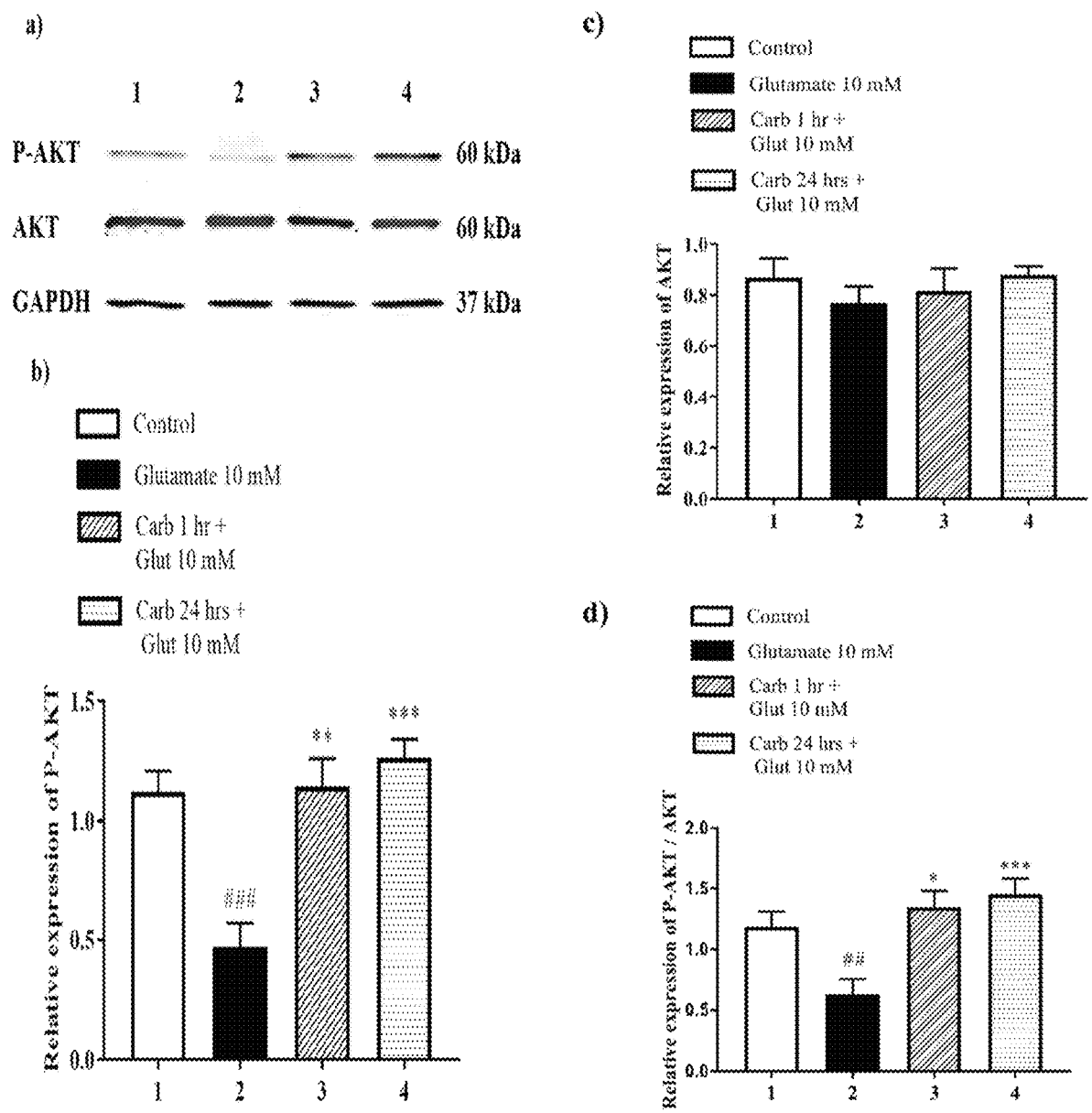
FIG. 3 is a Western blot (a) and graphs (b-d) showing AKT and P-AKT expression in PC-12 cells after glutamate exposure with or without treatment with carbamathione.
Figure 4:
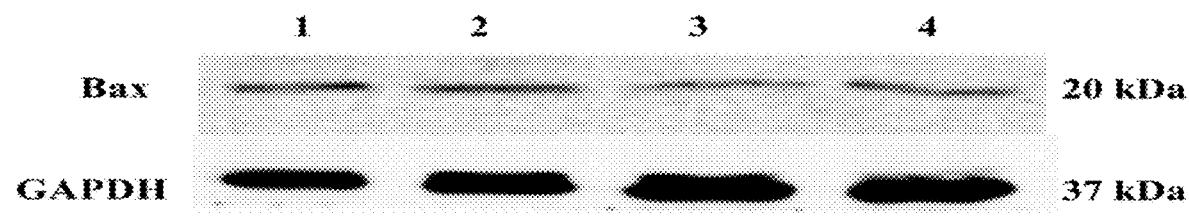
FIG. 4 is a Western blot (a) and graph (b) showing Bax expression in PC-12 cells after glutamate exposure with or without treatment with carbamathione.
Figure 4:
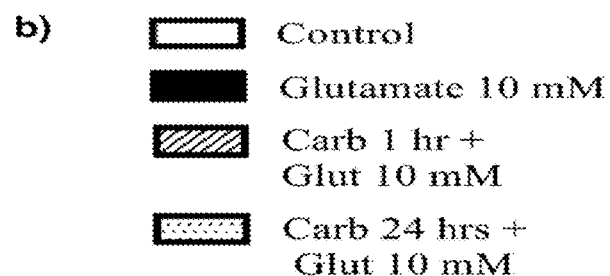
Figure 4:
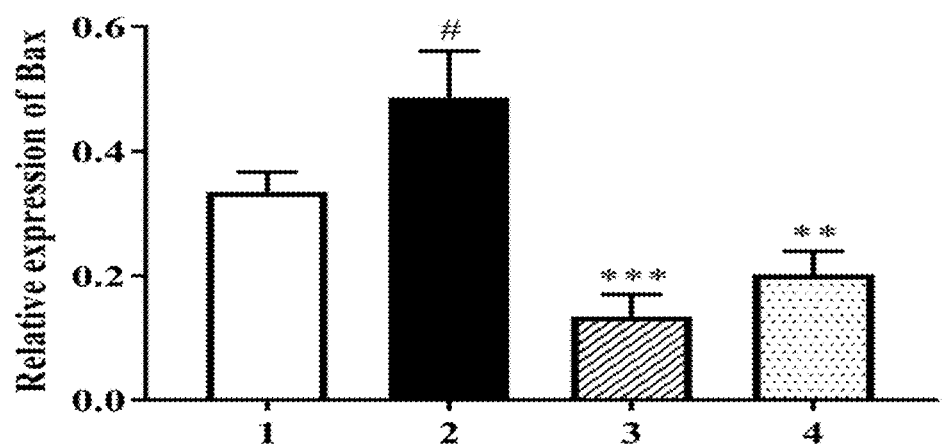
Figure 5:
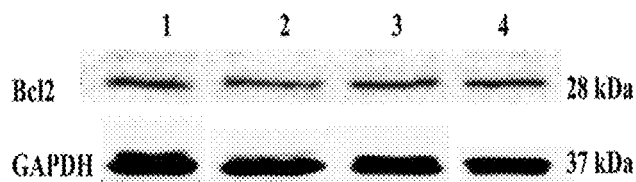
FIG. 5 is a Western blot (a) and graphs (b, c) showing Bcl2 expression in PC-12 cells after glutamate exposure with or without treatment with carbamathione.
Figure 5:
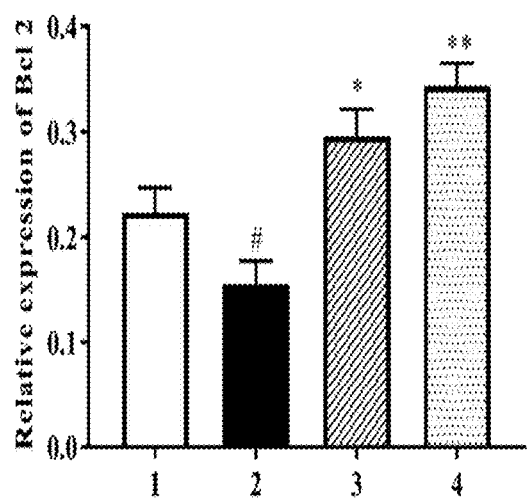
Figure 5:
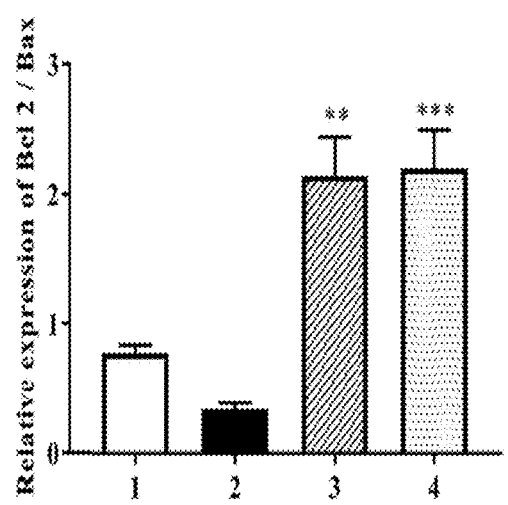
Figure 6:
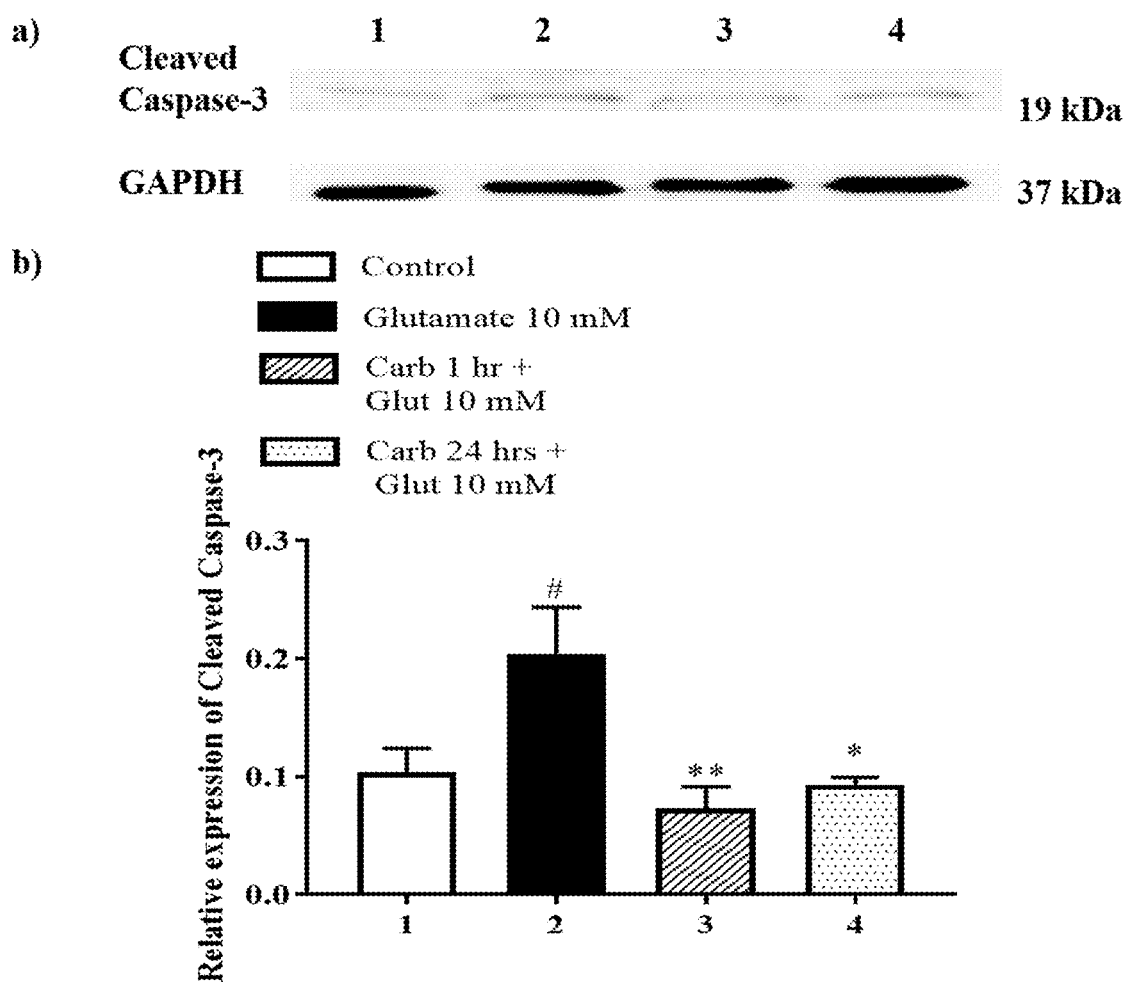
FIG. 6 is a Western blot (a) and graph (b) showing cleaved Caspase-3 expression in PC-12 cells after glutamate exposure with or without treatment with carbamathione.
Figure 7:
FIG. 7 is a Western blot (a) and graph (b) showing GRP-78 expression in PC-12 cells after glutamate exposure with or without treatment with carbamathione.
Figure 7:
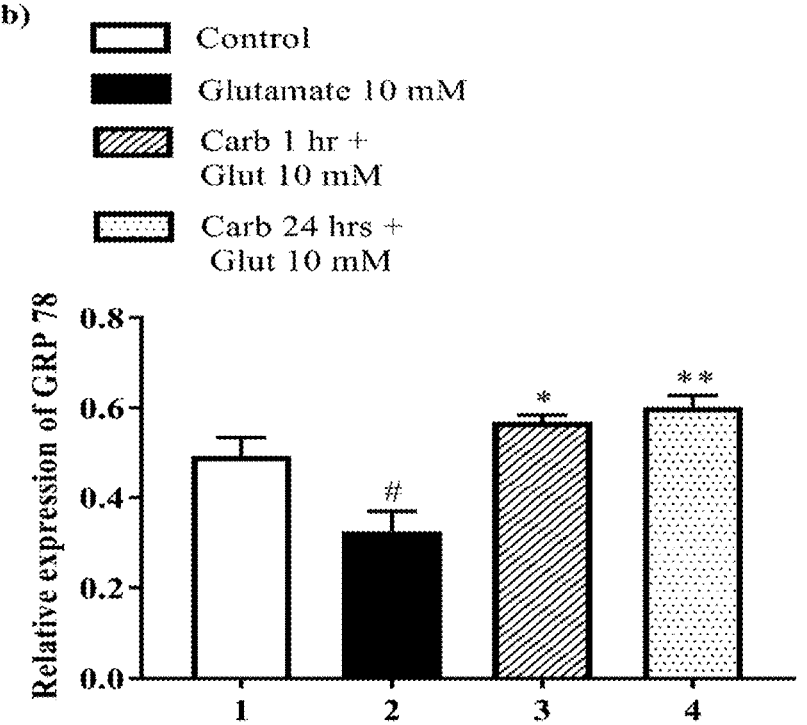
Figure 8:
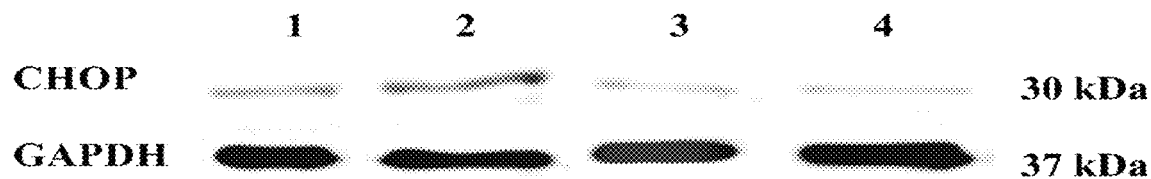
FIG. 8 is a Western blot (a) and graph (b) showing CHOP expression in PC-12 cells after glutamate exposure with or without treatment with carbamathione.
Figure 8:
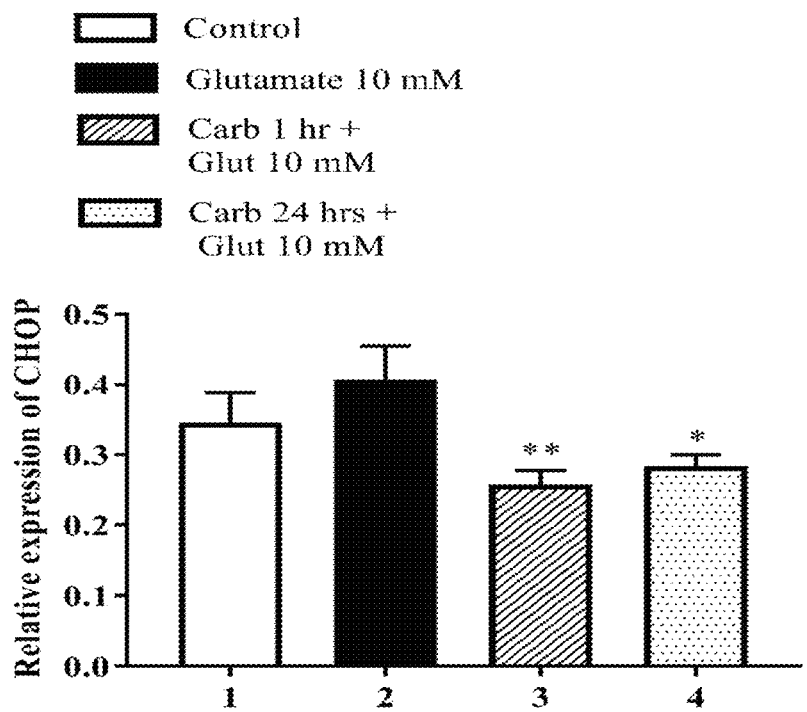

In other experiments, the effect of carbamathione on expression of the ER stress apoptotic marker CHOP, cell death marker cleaved caspase-3, Bax, Bcl2, P-AKT, GRP 78 and Hsp 27 in glutamate-treated PCT-12 cells was examined FIGS. 2-8 show the results of these experiments where PC-12 cells were exposed to 25 µM carbamathione for 1 or 24 h before 10 mM glutamate treatment for 24 h, whereafter Western blotting was performed. Referring to FIG. 2, carbamathione resulted in increased expression of Hsp 27 in carbamathione+glutamate-treated groups (1 hour and 24 hours) versus glutamate only-treated groups. Referring to FIG. 3, P-AKT (the activated form of AKT) showed a dramatic up-regulation in carbamathione+glutamate-treated groups (1 hour and 24 hours) versus glutamate only-treated groups, whereas AKT expression showed no changes when carbamathione was used. Referring to FIG. 4, carbamathione down-regulated the proapoptotic protein Bax in carbamathione+glutamate-treated groups (1 hour and 24 hours) versus glutamate only-treated groups. On the other hand, referring to FIG. 5, the anti-apoptotic protein Bcl2 showed an increase in the ratio of Bcl2/Bax in the carbamathione+glutamate-treated groups (1 hour and 24 hours) versus glutamate only-treated groups. Referring to FIG. 6, cleaved Caspase-3 was upregulated in carbamathione+glutamate-treated groups (1 hour and 24 hours) versus glutamate only-treated groups. Referring to FIG. 7, expression of GRP 78 protein, an ER stress marker, was upregulated in primary neurons after treatment with 10 mM glutamate for 24 hours. However, carbamathione restored the level of GRP 78 to control levels. Referring to FIG. 8, expression of C/EBP homologous protein (CHOP), another ER stress marker, was upregulated by glutamate. Carbamathione treatment restored CHOP expression to the control level.

Figure 9:
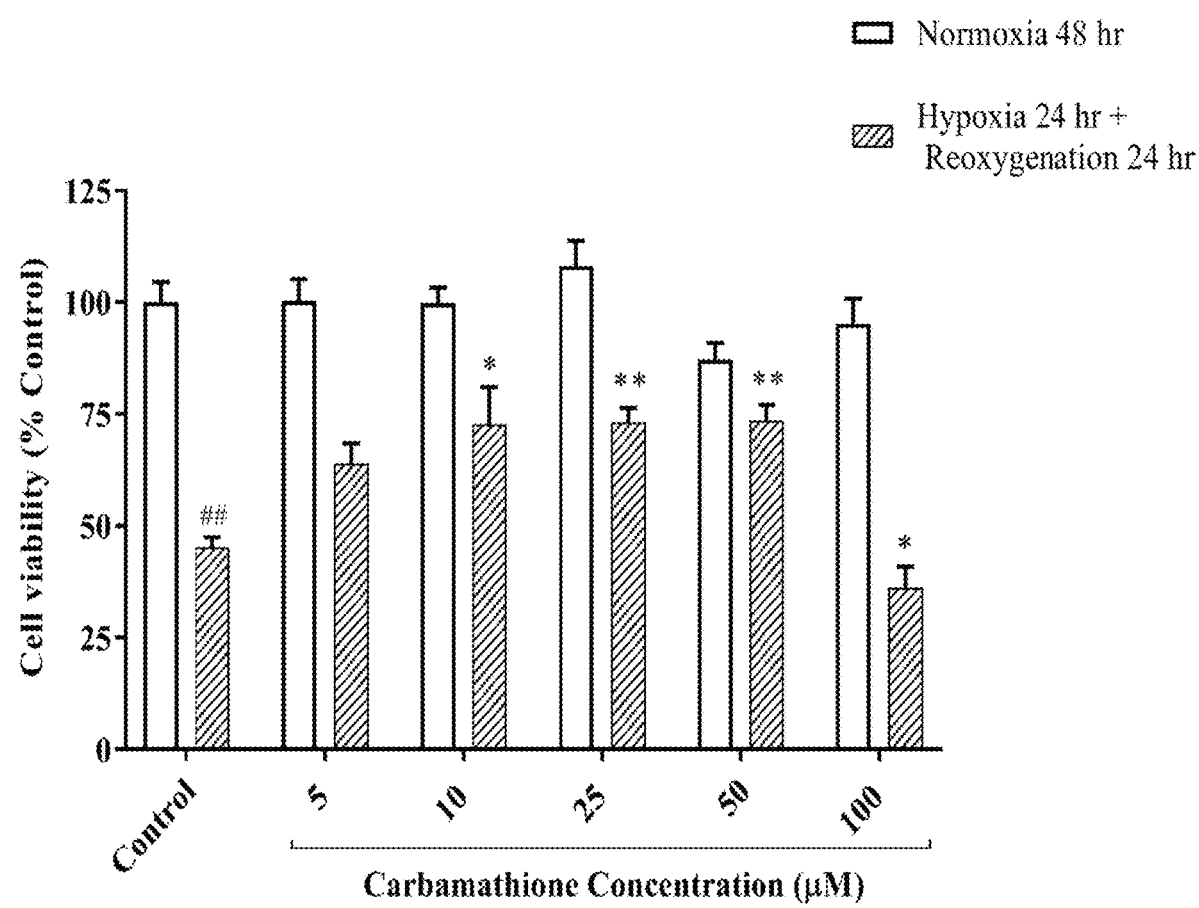
FIG. 9 is a graph showing the protective effects of carbamathione on PC-12 cells cultured under hypoxia/reoxygenation conditions.
Figure 10:
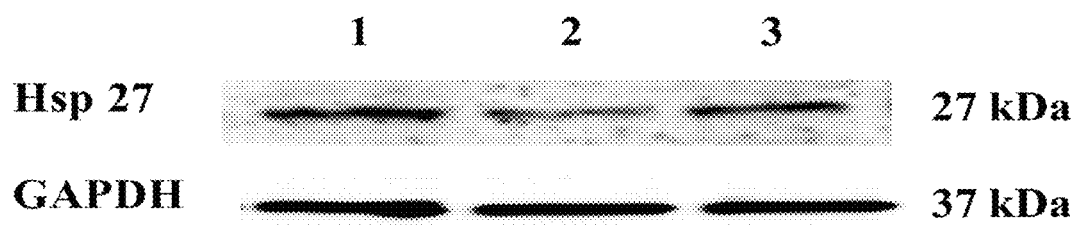
FIG. 10 is a Western blot (a) and graph (b) showing Hsp 27 expression in PC-12 cells cultured under hypoxia/reoxygenation conditions with or without treatment with carbamathione.
Figure 10:
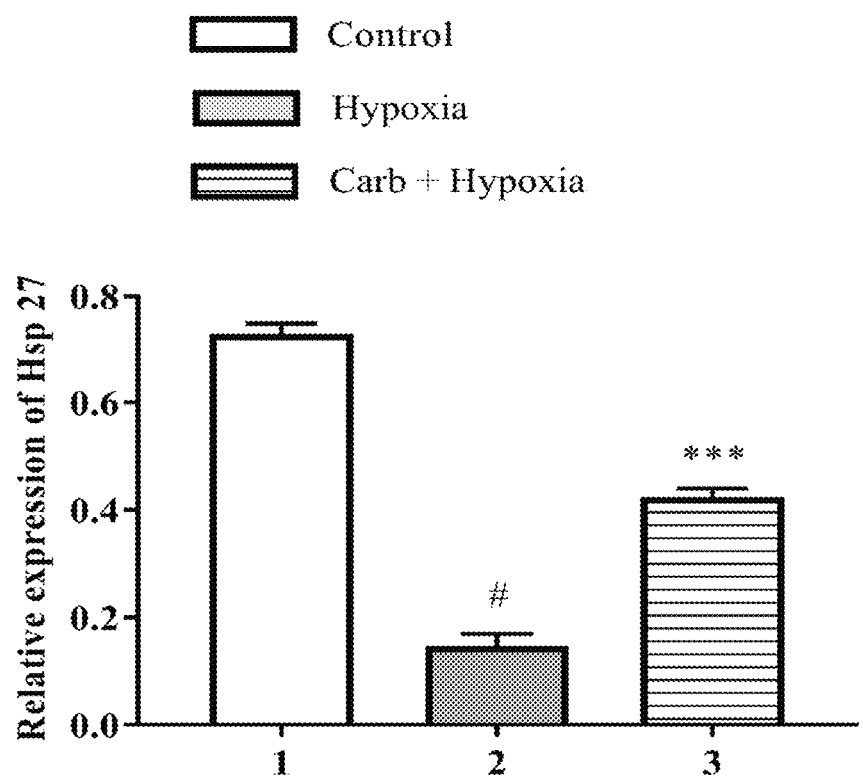
Figure 11:
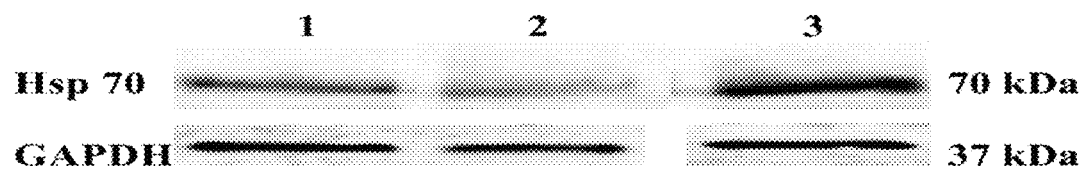
FIG. 11 is a Western blot (a) and graph (b) showing Hsp 70 expression in PC-12 cells cultured under hypoxia/reoxygenation conditions with or without treatment with carbamathione.
Figure 11:
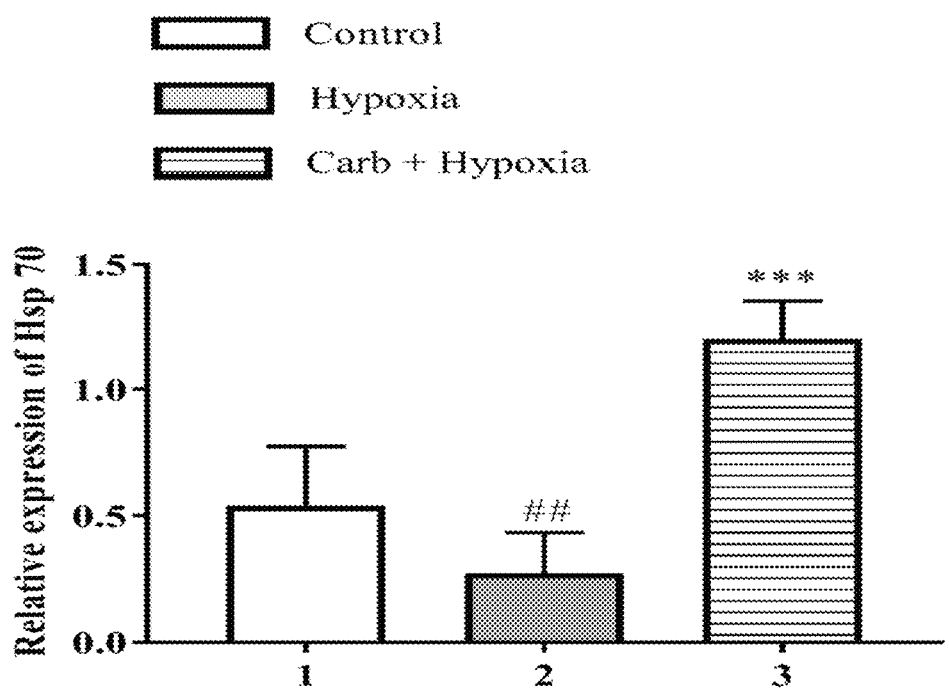
Figure 12:
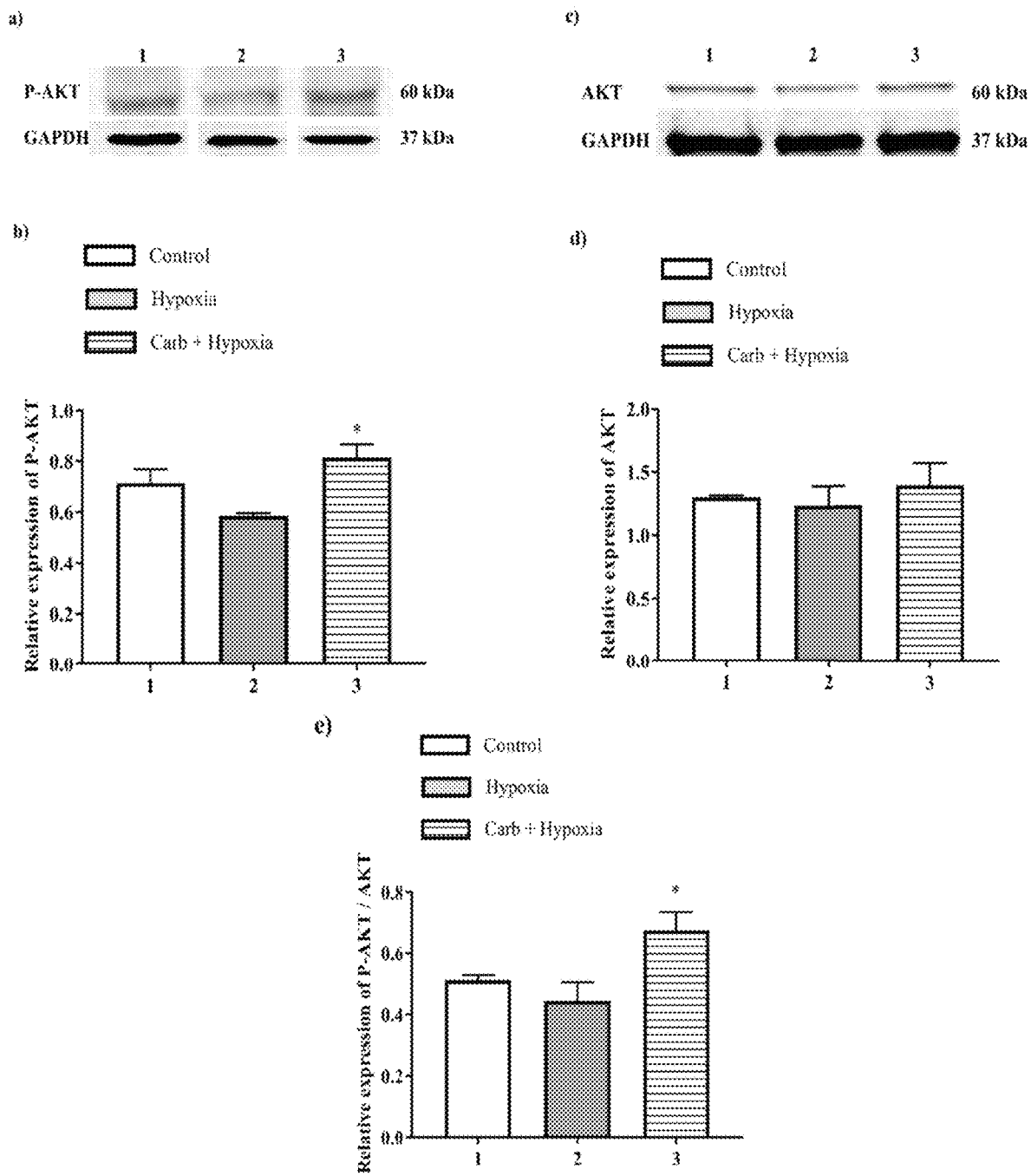
FIG. 12 is Western blots (a, c) and graphs (b, d, e) showing AKT and P-AKT expression in PC-12 cells cultured under hypoxia/reoxygenation conditions with or without treatment with carbamathione.
Figure 13:
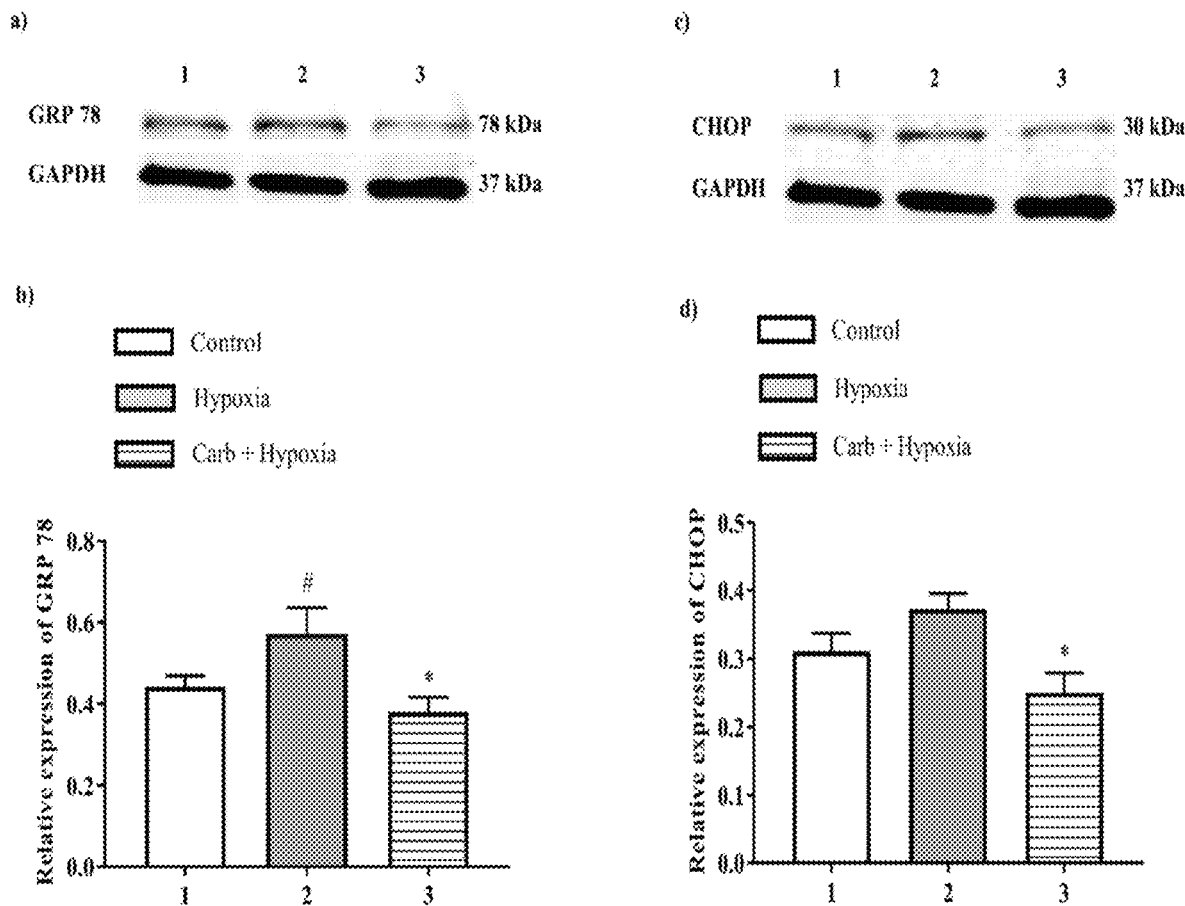
FIG. 13 is Western blots (a, c) and graphs (b, d) showing GRP 78 and CHOP expression in PC-12 cells cultured under hypoxia/reoxygenation conditions with or without treatment with carbamathione.
Figure 14:
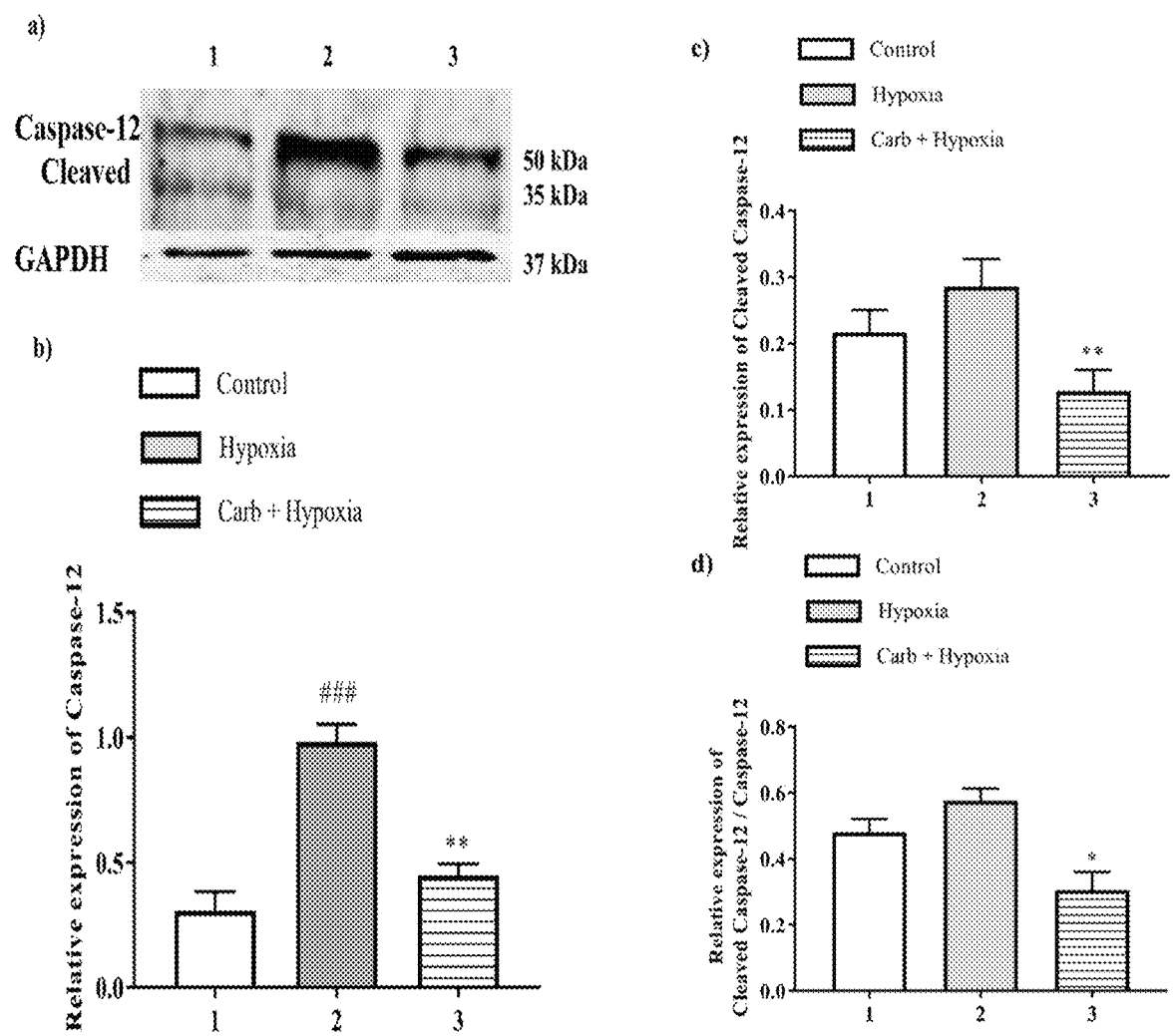
FIG. 14 is Western blots (a, c) and graphs (b, d) showing Caspase-12 and cleaved Caspase-12 expression in PC-12 cells cultured under hypoxia/reoxygenation conditions with or without treatment with carbamathione.

In another set of experiments, the effect of carbamathione on cell viability and expression of various biomarkers in PCT-12 cells exposed to hypoxia/reoxygenation was evaluated. Referring to FIG. 9, PC-12 cells were exposed to hypoxia and reoxygenation in the presence or in the absence of 5-100 µM carbamathione. After hypoxia and reoxygenation, ATP levels for cells without carbamathione treatment dropped to about 47% (percentage of control), whereas carbamathione treatment dramatically increased the cell viability. As shown in FIGS. 10 and 11, the heat shock proteins, Hsp 27 and Hsp 70, showed greater over-expression in the carbamathione+hypoxia-reoxygenation groups compared to hypoxia-reoxygenation alone groups. Referring to FIG. 12, P-AKT was up-regulated in the carbamathione+hypoxia-reoxygenation groups compared to hypoxia-reoxygenation alone groups, whereas AKT expression showed no changes when carbamathione was used. Referring to FIGS. 13 and 14, GRP 78, CHOP, Caspase-12, and cleaved Caspase-12 expression induced by hypoxia-reoxygenation were each inhibited by carbamathione. These results demonstrate that carbamathione has ability to inhibit the apoptosis induced by ER stress in hypoxia/reoxygenation.

Figure 15:
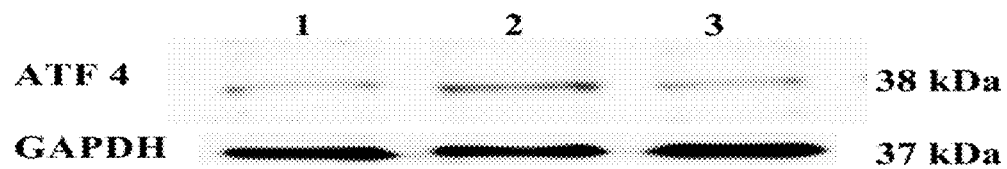
FIG. 15 is a Western blot (a) and graph (b) showing ATF 4 expression in PC-12 cells cultured under hypoxia/reoxygenation conditions with or without treatment with carbamathione.
Figure 15:
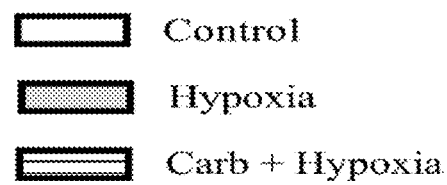
Figure 15:
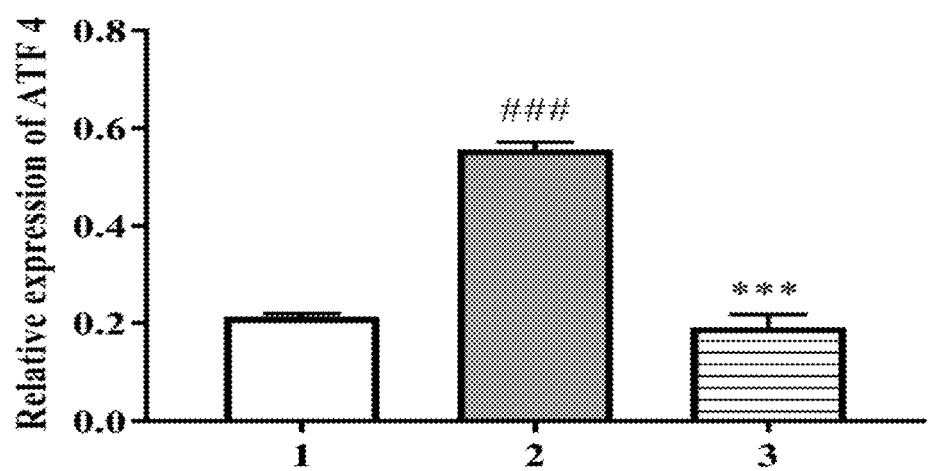
Figure 16:
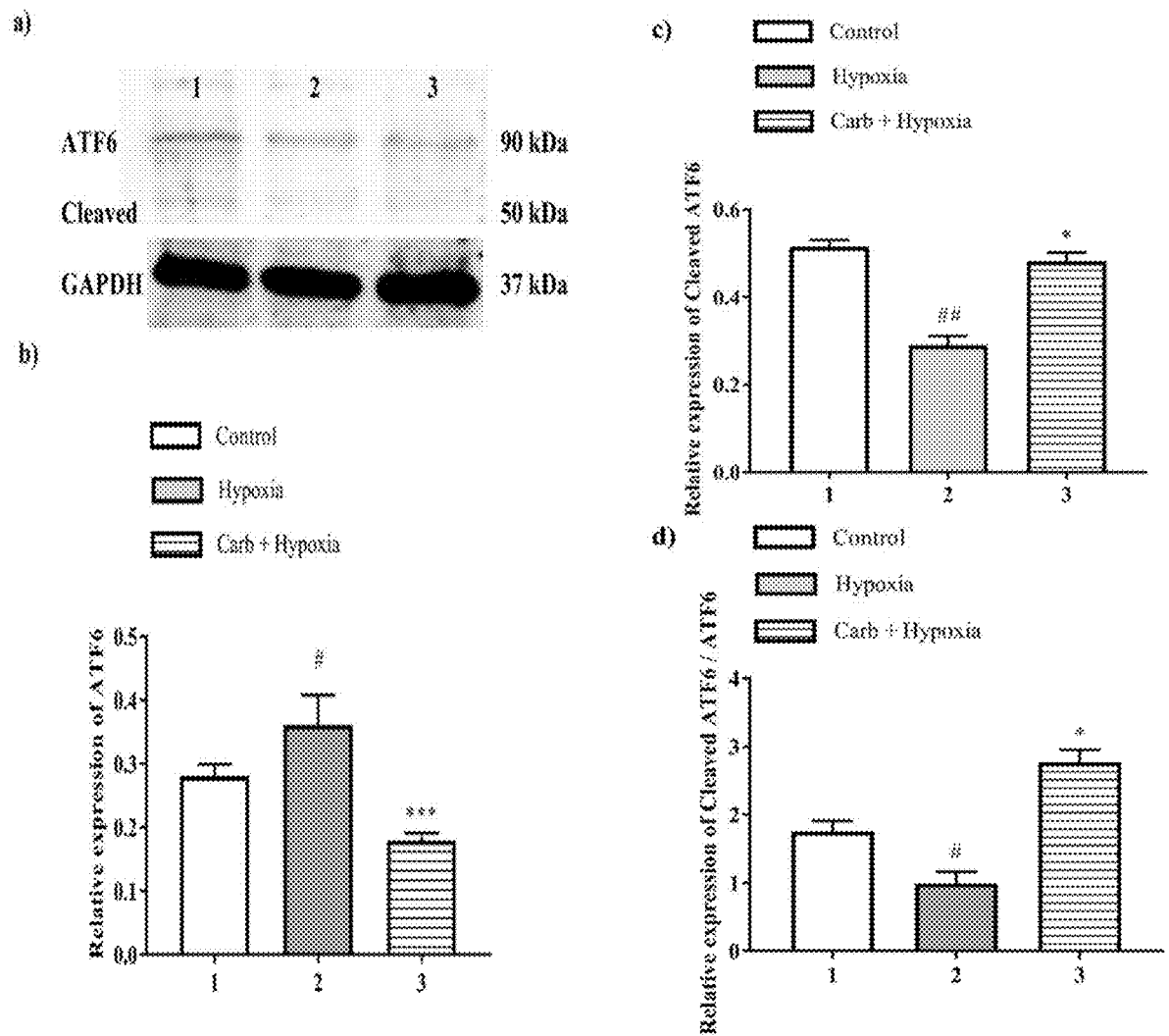
FIG. 16 is a Western blot (a) and graphs (b-d) showing ATF 6 expression in PC-12 cells cultured under hypoxia/reoxygenation conditions with or without treatment with carbamathione.
Figure 17:
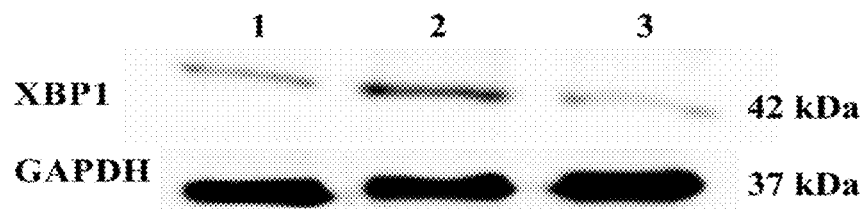
FIG. 17 is a Western blot (a) and graph (b) showing XBP1 expression in PC-12 cells cultured under hypoxia/reoxygenation conditions with or without treatment with carbamathione.
Figure 17:
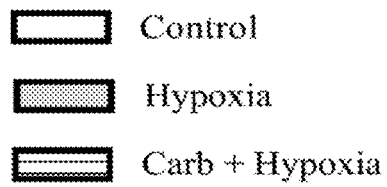
Figure 17:
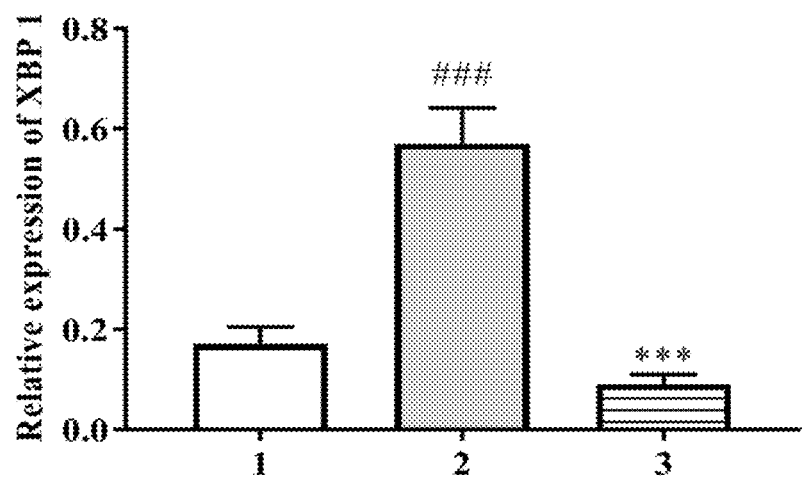

As shown in FIGS. 15-17, expression of the ER stress markers ATF4, ATF6, and XBP1 induced by hypoxia-reoxygenation were each inhibited by carbamathione. These results indicate that carbamathione inhibited initiation of the PERK, ATF6, and IRE1 ER stress pathways induced by hypoxia/reoxygenation.

Figure 18:
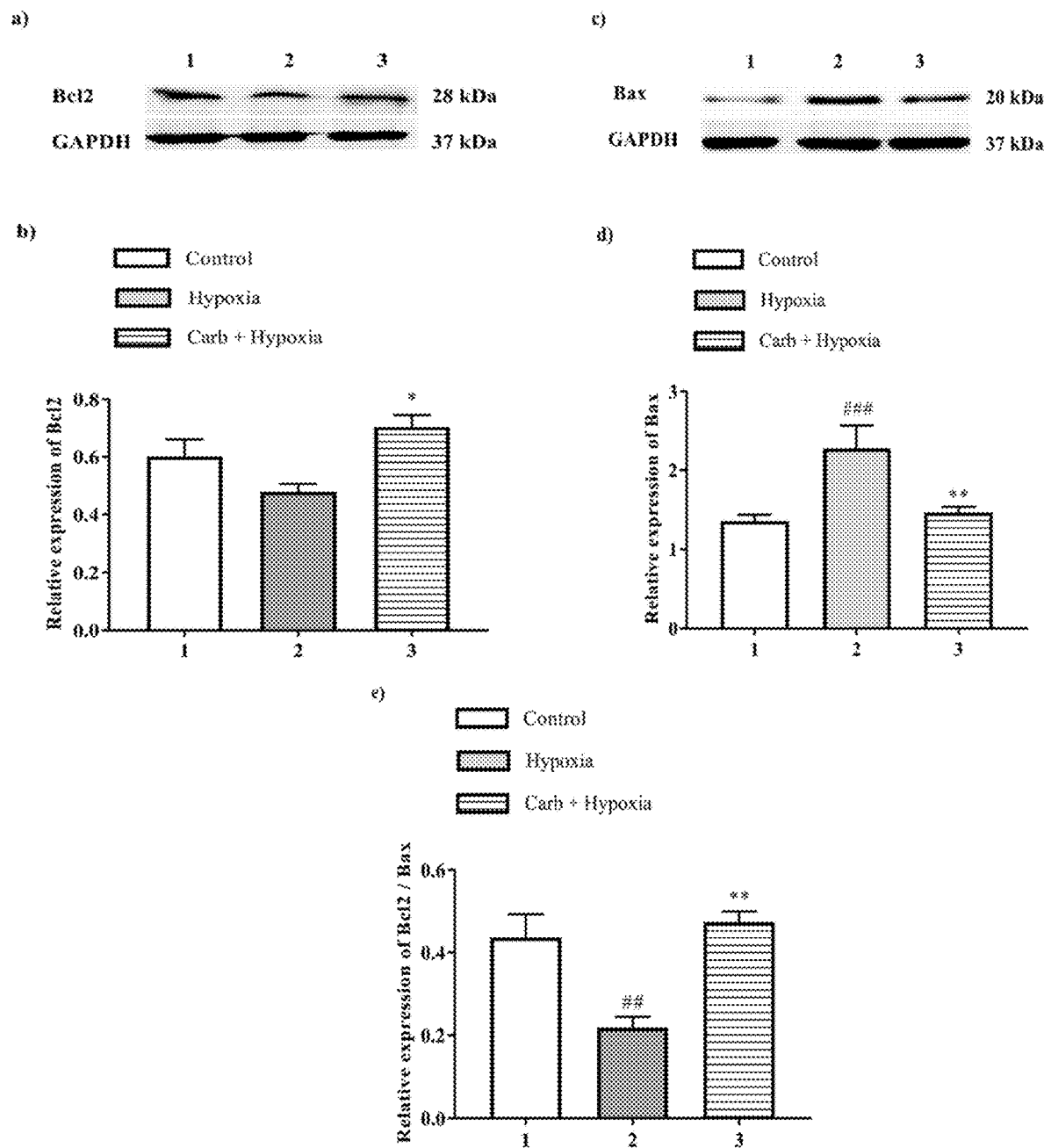
FIG. 18 is Western blots (a, c) and graphs (b, d, e) showing Bcl2 and Bax expression in PC-12 cells cultured under hypoxia/reoxygenation conditions with or without treatment with carbamathione.
Figure 19:
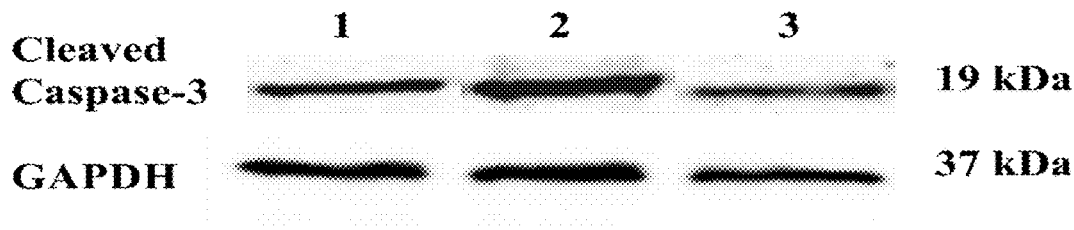
FIG. 19 is a Western blot (a) and graph (b) showing cleaved Caspase-3 expression in PC-12 cells cultured under hypoxia/reoxygenation conditions with or without treatment with carbamathione.
Figure 19:
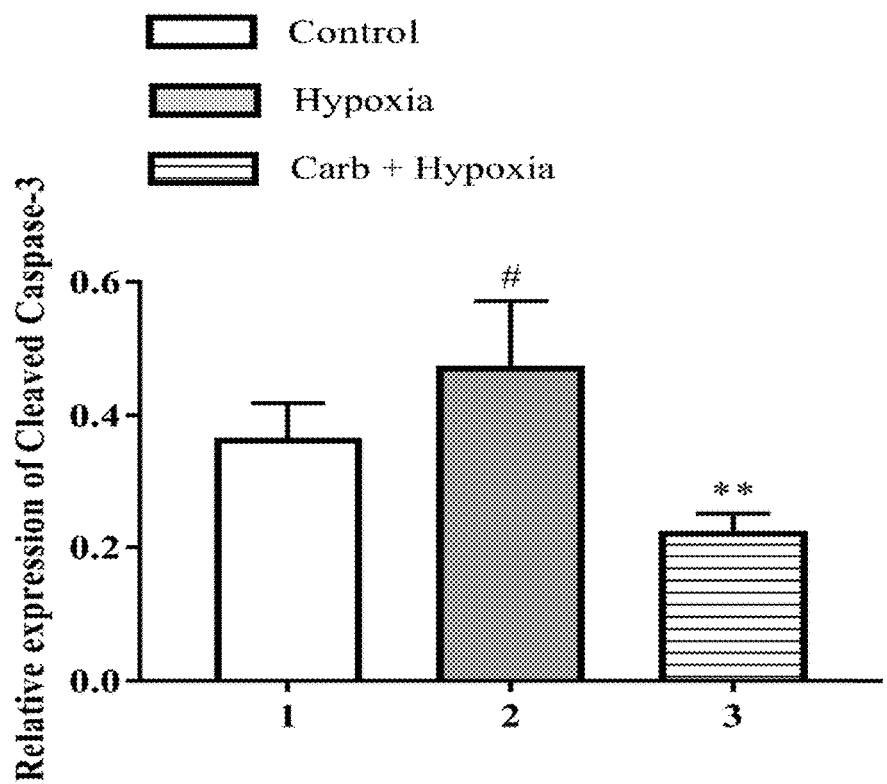

Referring to FIGS. 18 and 19, carbamathione treatment increased the downregulation of Bcl2 induced by hypoxia/reoxygenation and decreased the upregulation of Bax and cleaved Caspase-3 induced by hypoxia/reoxygenation. Hypoxia/reoxygenation induced changes in Bcl2 and Bax levels resulted in a decrease in the Bcl2:Bax ratio, which was inhibited in the carbamathione-treated cells. These results indicate that carbamathione reduces pro-apoptotic signaling induced by hypoxia/reoxygenation.

Figure 20:
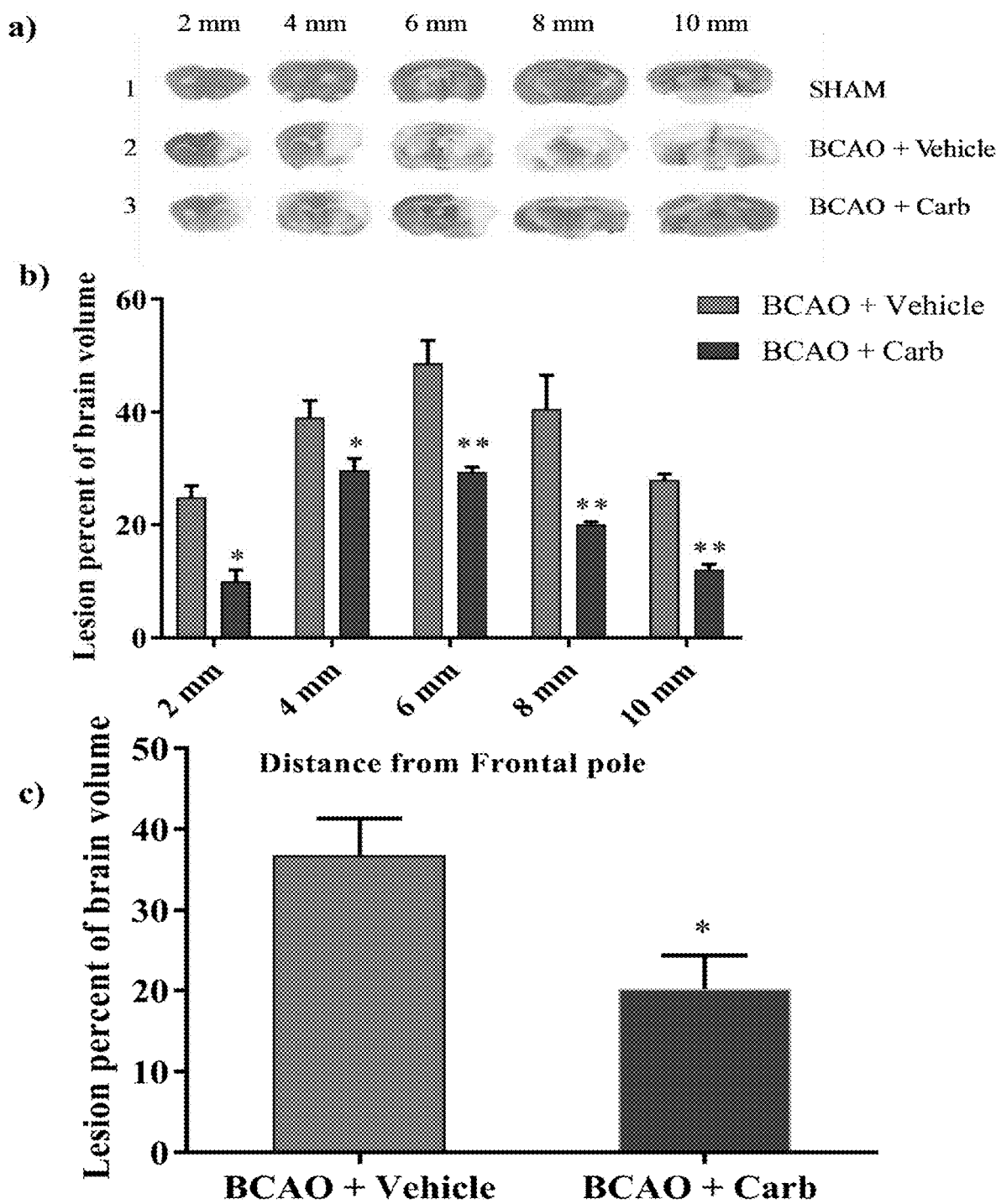
FIG. 20 is a series of photographs (a) and graphs (b, c) showing the effect of carbamathione on ischemia-induced brain injury in a BCAO stroke model.

Animal experiments to test the effect of carbamathione on reperfusion brain injury were also undertaken. As shown in FIG. 20, brain infarcts that developed in BCAO mice were evaluated using TTC staining where the infarct size at 2, 4, 6, 8, and 10 mm from the frontal pole was assessed. The infarct size was noticeably reduced in the mice treated with carbamathione. FIG. 20c represents mean infarct volumes resulting from 30 min of transient BCAO in groups. Carbamathione markedly reduced the volume of the lesion of the sections 2, 4, 6, 8 and 10 mm when carbamathione was injected 30 min after occlusion. The sham-operated group showed no ischemic injury.

Figure 21:
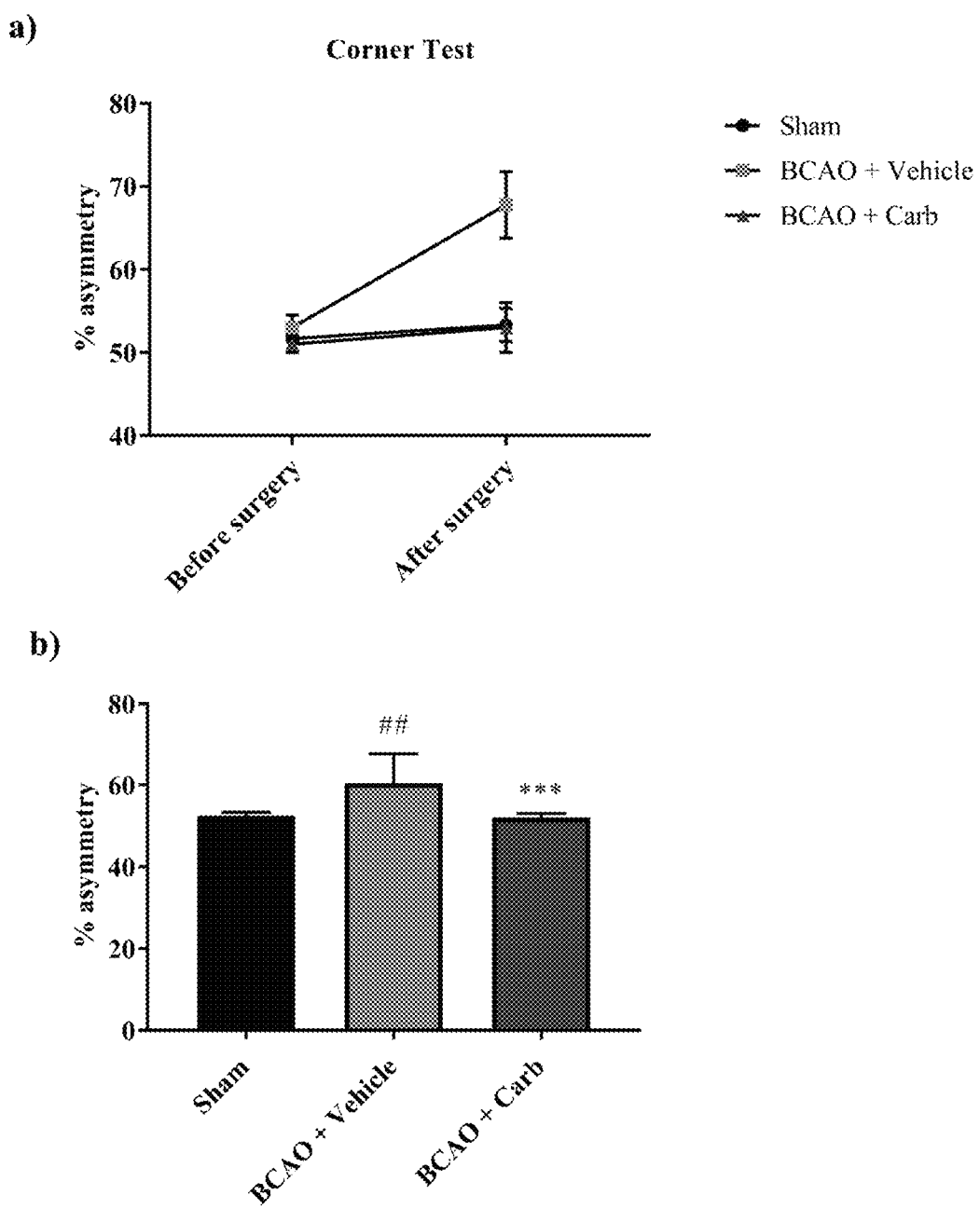
FIG. 21 is two graphs (a, b) showing the effect of carbamathione on the Corner test in ischemia-induced brain injury in a BCAO stroke model.

Referring to FIG. 21, the Corner test was used to determine the subject animals' asymmetric direction of turning when encountering a corner an indicator of brain injury. An experimental corner composed of two boards (30×20×1 $cm^3$) arranged to form 30° corner was set up, and the rate of turns when normal mice faced a 30° corner (i.e., turning to either the left or right) was determined to be 50±8% (symmetric and no bias) before BCAO-30 min surgery. Mice were measured before sacrifice at 4 days after the BCAO-30 procedure. A significant increase in asymmetric turning (~90% to one side) in BCAO-30 mice when facing a 30° corner was noted. BCAO mice without treatment showed significant asymmetric turning (~90%) beginning one day after the procedure and persisting for at least four days. Mice with treatment (BCAO+carbamathione), on the other hand, exhibited behavior not significant differently from that seen in the sham-operated mice.

Figure 22:
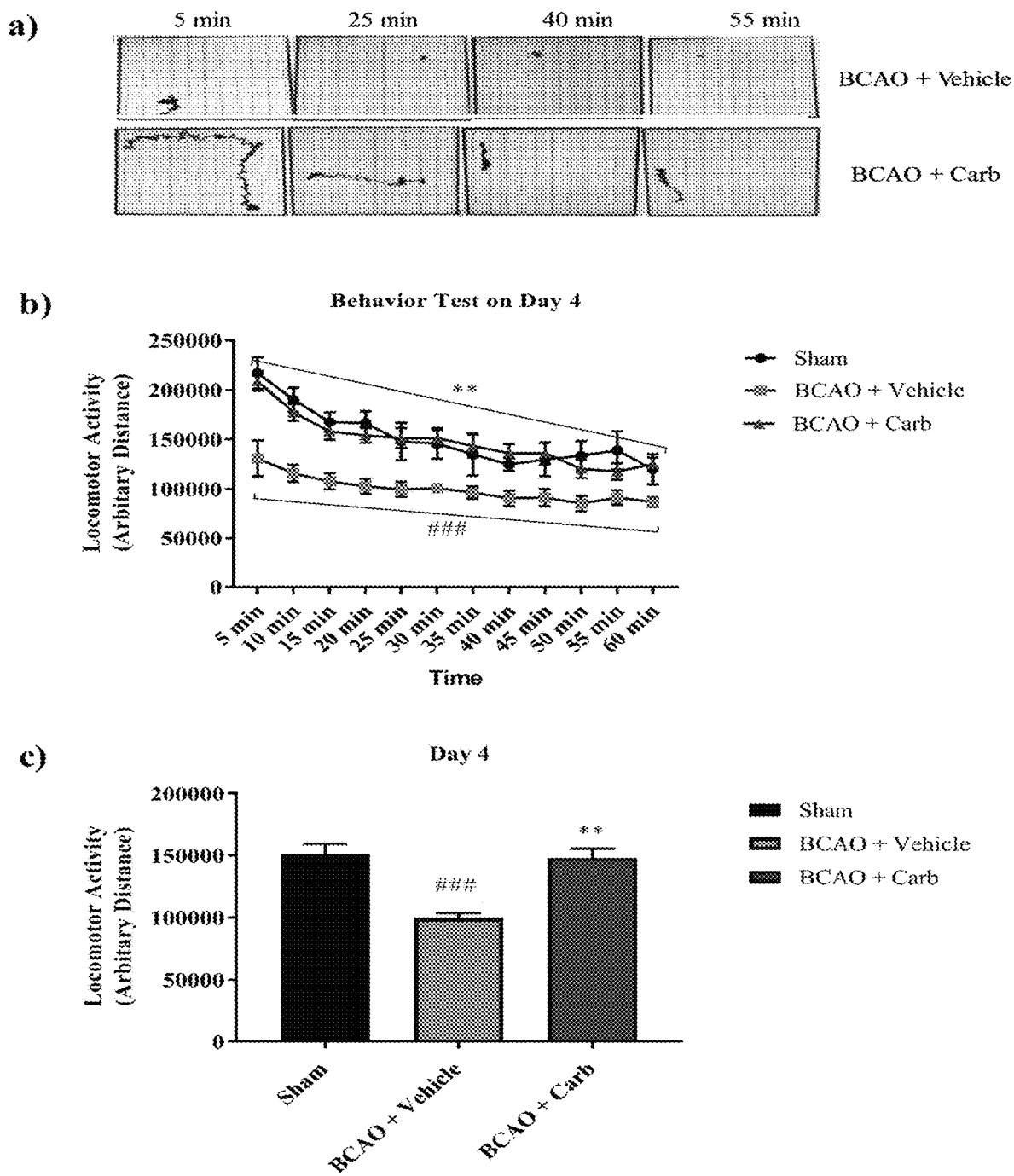
FIG. 22 is samples traces (a) and graphs (b, c) showing the effect of carbamathione on locomotor activity in ischemia-induced brain injury in a BCAO stroke model.

Referring to FIG. 22, to test whether motor dysfunction might contribute to the learning deficits observed in the Corner test, the locomotor activity of mice was measured on a force-plate actometer. A similar difference in behavior between sham group and BCAO with carbamathione treated group was observed. The locomotor activity of the sham and BCAO with carbamathione groups were statistically significantly different than BCAO with vehicle group.

Figure 23:
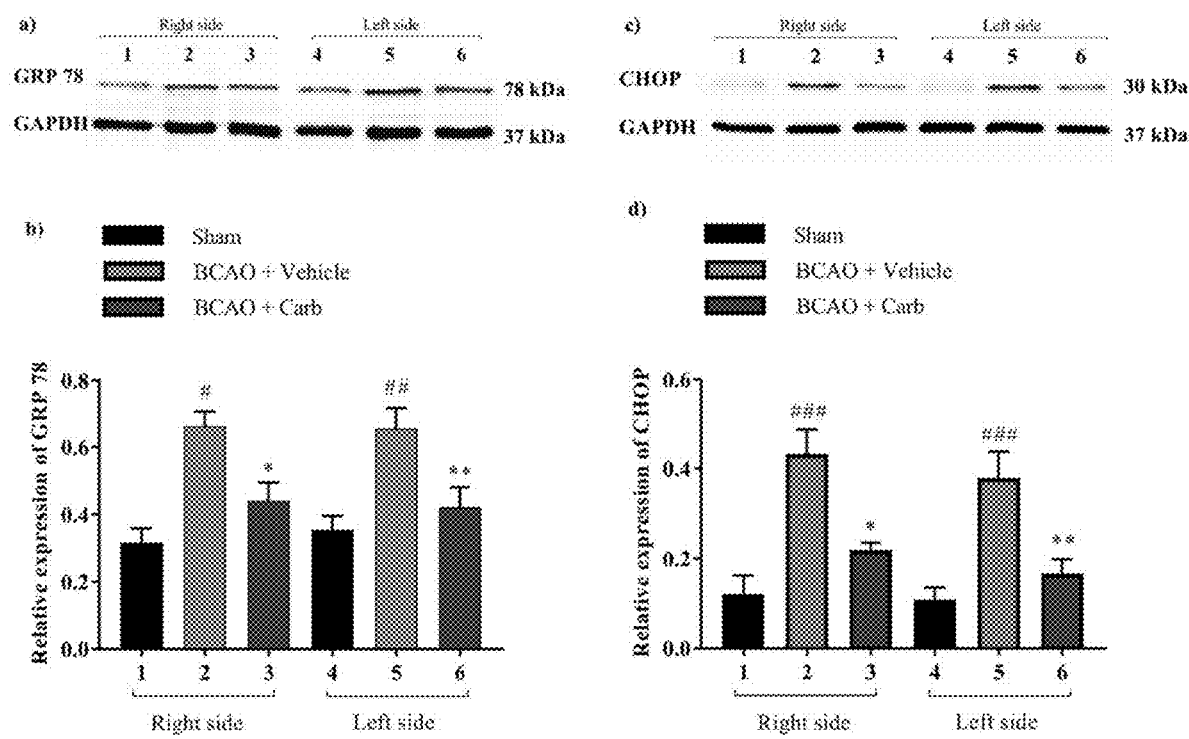
FIG. 23 is Western blots (a, c) and graphs (b, d) showing the effect of carbamathione on UPR (GRP 78) and CHOP expression in ischemia-induced brain injury in a BCAO stroke model.
Figure 24:
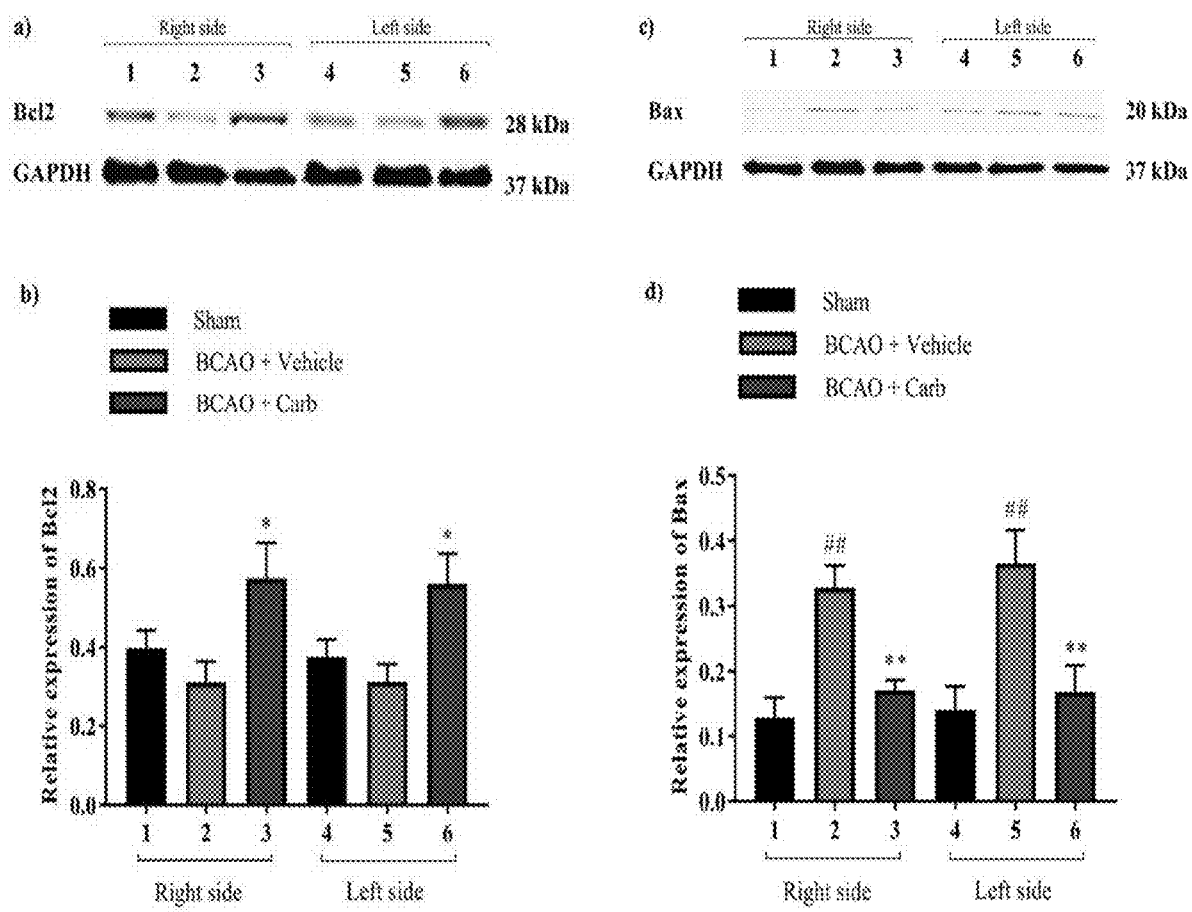
FIG. 24 is Western blots (a, c) and graphs (b, d) showing the effect of carbamathione on Bcl2 and BAX expression in ischemia-induced brain injury in a BCAO stroke model.
Figure 25:
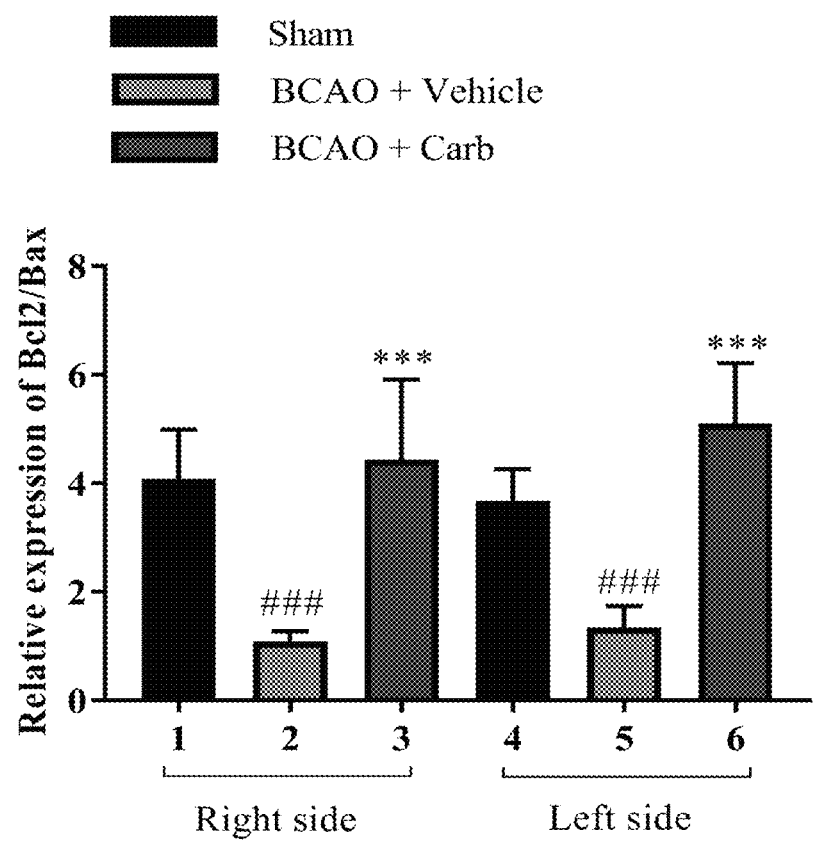
FIG. 25 is a graph showing the effect of carbamathione on Bcl2/BAX ratio expression in ischemia-induced right and left brain injury in a BCAO stroke model.

As shown in FIG. 23, after BCAO, GRP 78 and CHOP expression in the brains of the carbamathione-treated group decreased dramatically after 4 days compared to vehicle treated group. And, as shown in FIG. 24, compared with the vehicle treated group, the carbamathione-treated group exhibited significantly increased expression of Bcl2 and decreased expression of at day 4 post BCAO. The Bcl2/Bax ratios are shown in FIG. 25.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of minimizing the size of a brain infarct that develops in a mammalian subject in response to a cerebral ischemia/reperfusion injury, the method comprising the step of administering to the subject a carbamathione agent, wherein the amount of the carbamathione agent is effective for minimizing the size of a brain infarct that develops in the mammalian subject as a result of the cerebral ischemia/reperfusion injury.

2. The method of claim 1, wherein the subject has been diagnosed with ischemic stroke prior to the administration step.

3. The method of claim 1, wherein the subject has been administered tissue plasminogen activator.

4. The method of claim 1, wherein the carbamathione agent is comprised within a pharmaceutical composition formulated for injection.

5. The method of claim 1, wherein the carbamathione agent is administered to the subject within 24 hours of the onset of symptoms of ischemic stroke.

6. The method of claim 1, wherein the carbamathione agent is repeatedly administered to the subject at least once per day for at least 3 days.

7. The method of claim 1, wherein the carbamathione agent is repeatedly administered to the subject for at least 7 days.

8. The method of claim 1, wherein the carbamathione agent is repeatedly administered at least until the infarct becomes at least 50% fibrotic.

\* \* \* \* \*